United States Patent
Ji et al.

(10) Patent No.: US 10,646,483 B2
(45) Date of Patent: May 12, 2020

(54) CRYSTAL FORM OF IMIDAZOLONE TYPE COMPOUNDS, AND PREPARATION METHOD, PHARMACEUTICAL COMPOSITION AND USE THEREOF

(71) Applicant: Foreland Pharma Co., Ltd., Beijing (CN)

(72) Inventors: Qi Ji, Beijing (CN); Zhenjian Du, Beijing (CN); Xingmin Zhang, Beijing (CN); Lei Wang, Beijing (CN); Congmin Gao, Beijing (CN); Longlong Gong, Beijing (CN)

(73) Assignee: Foreland Pharma Co., Ltd., Beijing (CN)

( * ) Notice: Subject to any disclaimer, the term of this patent is extended or adjusted under 35 U.S.C. 154(b) by 0 days.

(21) Appl. No.: 16/064,242

(22) PCT Filed: Jan. 26, 2016

(86) PCT No.: PCT/CN2016/072179
§ 371 (c)(1),
(2) Date: Jun. 20, 2018

(87) PCT Pub. No.: WO2017/128042
PCT Pub. Date: Aug. 3, 2017

(65) Prior Publication Data
US 2018/0369233 A1  Dec. 27, 2018

(51) Int. Cl.
*C07D 471/04* (2006.01)
*C07D 471/14* (2006.01)
*A61K 31/4745* (2006.01)
*A61P 35/00* (2006.01)

(52) U.S. Cl.
CPC .......... *A61K 31/4745* (2013.01); *A61P 35/00* (2018.01); *C07D 471/04* (2013.01); *C07D 471/14* (2013.01)

(58) Field of Classification Search
CPC .............................. C07D 471/04; C07D 471/14
See application file for complete search history.

(56) References Cited

U.S. PATENT DOCUMENTS 10,047,084 B2 * 8/2018 Zhang .................. C07D 471/04

FOREIGN PATENT DOCUMENTS

| EP | 3072893 A1 | 9/2016 |
| WO | 2015074516 A1 | 5/2015 |

* cited by examiner

*Primary Examiner* — Rebecca L Anderson
(74) *Attorney, Agent, or Firm* — Fox Rothschild LLP

(57) ABSTRACT

The present invention relates to the crystal form of imidazolone type compounds, and a preparation method, pharmaceutical composition and use thereof, and falls within the field of pharmaceutical compound crystals. The crystal form provided by the present invention has a good stability, comprising good stability under the three extreme conditions of high temperature, high humidity and strong illumination, and can also maintain a good stability during the tablet compressing process. The crystal form provided by the present invention has good absorption and metabolism properties in vivo, comprising the drug concentration of blood, the drug concentration-time curve AUC, the half-life period, etc. In addition, the dissolving rate of the crystal form of the present invention is improved, wherein same is beneficial for the applications thereof in preparations.

18 Claims, 19 Drawing Sheets

CRYSTAL FORM OF IMIDAZOLONE TYPE COMPOUNDS, AND PREPARATION METHOD, PHARMACEUTICAL COMPOSITION AND USE THEREOF

TECHNICAL FIELD

The present invention relates to crystal forms of an imidazolone compound having a PI3K/mTOR dual inhibitory activity, and preparation method, pharmaceutical composition and use thereof, and pertains to the field of pharmaceutical compound crystals.

BACKGROUND ART

Mammalian target of rapamycin (mTOR) is an atypical serine/threonine protein kinase, is a member of the phosphoinositide 3-kinase (PI3K) related kinase family, and is a main signaling molecule of cell functions such as intracellular synthesis and catabolism. The mTOR signaling pathway has a close relationship with nutrition, energy states and growth factors, and modulates many cellular processes including autophagy, protein, lipids and lysosomes synthesis and energy metabolism, cytoskeleton organization, cell survival, and so on. Under the changing peripheral nutritional conditions of mammalian cells, mTOR regulates the conversion between synthesis and degradation metabolism to enable the cells to grow and survive under different nutritional conditions. Because of the important role of mTOR in cells, aberrant or deregulated mTOR signaling can lead to human diseases (such as cancer and other diseases). Therefore, the mTOR signaling pathway is becoming an important target for the design of anticancer drugs.

The activation of the PI3K/Akt/mTOR signaling pathway is closely related to a variety of tumorigenesis. mTOR can accelerate cell cycles, reduce apoptosis and promote tumor cell migration in brain glioma, breast cancer, and ovarian cancer. Activation of mTOR begins at several ligand-activated growth factor receptors on the cell surface, such as epidermal growth factor receptor and insulin-like growth factor-1 and -2 (IGF-1 and IGF-2). The activation of the receptors leads to the activation of the PI3K kinase, thereby resulting in the activation of the downstream effector Akt protein. Akt is a regulatory factor that can regulate cell survival in multiple levels. After phosphorylation, Aid inhibits the downstream TSC1/2 complex, and thus mTOR is activated by Rheb. Downstream the PI3K/Akt and PEN/Akt and Ras/Erk1/2 signaling pathways, the TSC1/2 complex plays a vital role in the regulation of mTOR activation.

Two different mTOR protein complexes, i.e., mTORC1 and mTORC2, have been found in cells. Both protein complexes contain a unique protein interacting with mTOR, and are regulated by different mechanisms, respectively. Great progress has been made in the research and development of mTOR inhibitor drugs. Rapamycin is the first discovered mTOR inhibitor and has shown good tumor-inhibiting effects in a variety of cancer models. Although rapamycin analogues with better pharmacological properties have been developed, clinically applicable rapamycin analogues are only confined to a few cancers. The important discovery that Aid is an important kinase in the survival of cancer cells and mTORC2 can directly phosphorylate Aid provides a new way of thinking in the anti-cancer research with mTORC2, and at the same time contributes to the research and development of the second-generation anti-cancer drugs which act on both mTORC1 and mTORC2 targets. Simultaneous inhibition of the activities of both mTOR complexes (mTORC1 and mTORC2) in cancer cells provides a wider and more effective anti-cancer effect.

Compound 1, which has the chemical name of 1-((1s,4s)-4-hydroxycyclohexyl)-3-methyl-8-(6-(1-methyl-1H-pyrazol-4-yl)pyridin-3-yl)-1H-imidazo[4,5-c]quinolin-2(3H)-one, is a dual inhibitor of protein kinases PI3K/mTOR, and has a structure represented by the following formula:

Compound 1

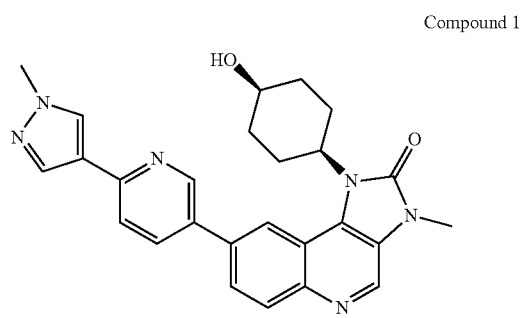 [SMILES: Cn1cc(-c2ccc(-c3ccc4ncc5c(c4c3)n([C@H]3CC[C@@H](O)CC3)c(=O)n5C)cn2)cn1]

Compound 1 and pharmaceutically acceptable salts thereof have been disclosed in WO 2015074516 A1, which report that they exhibit a good drug activity in cells and animal models. Therefore, the development of crystal forms of Compound 1 that are more stable, more suitable for formulation, and have better absorption and metabolism is of great significance for their clinical application.

SUMMARY OF THE INVENTION

The present invention provides a crystal of a pharmaceutically acceptable salt (e.g., a hydrochloride salt) of Compound 1 represented by the following formula or a hydrate thereof:

Compound 1

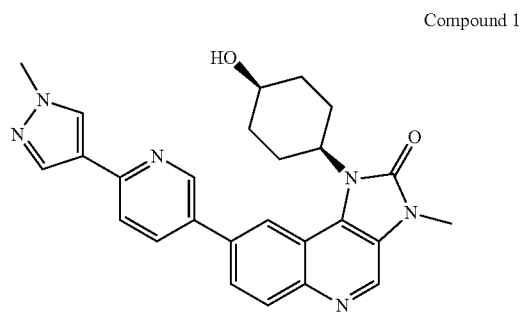 [SMILES: Cn1cc(-c2ccc(-c3ccc4ncc5c(c4c3)n([C@H]3CC[C@@H](O)CC3)c(=O)n5C)cn2)cn1]

The nomenclature of Compound 1 is 1-((1s,4s)-4-hydroxycyclohexyl)-3-methyl-8-(6-(1-methyl-1H-pyrazol-4-yl)pyridin-3-yl)-1H-imidazo[4,5-c]quinoline-2(3H)-one.
The methods for preparing Compound 1 and hydrochloride salt thereof are described in, for example, Example 18 of WO 2015074516 A1, which is incorporated herein by reference in its entirety.

The present invention provides Crystal Form I of Compound 1 hydrochloride monohydrate, which is characterized by an X-ray powder diffraction pattern obtained by using Cu-Kα radiation which may comprise characteristic peaks expressed in 2-theta angle (°) at 9.028±0.2, 11.196±0.2, 17.393±0.2, 22.504±0.2.

According to the present invention, the X-ray powder diffraction pattern of Crystal Form I obtained by using Cu-Kα radiation may comprise characteristic peaks expressed in 2-theta angle (°) at 9.028±0.2, 11.196±0.2, 15.406±0.2, 16.380±0.2, 17.393±0.2, 18.066±0.2, 18.739±0.2, 20.894±0.2, 22.504±0.2, 22.955±0.2.

Preferably, the X-ray powder diffraction pattern of Crystal Form I obtained by using Cu-Kα radiation comprises characteristic peaks expressed in 2-theta angle (°) at 9.028±0.2, 11.196±0.2, 15.406±0.2, 16.380±0.2, 17.393±0.2, 18.066±0.2, 18.739±0.2, 20.894±0.2, 22.504±0.2, 22.955±0.2, 26.312±0.2, 26.918±0.2, 27.556±0.2, 35.168±0.2.

More preferably, the X-ray powder diffraction pattern of Crystal Form I obtained by using Cu-Kα radiation comprises characteristic peaks expressed in 2-theta angle (°) at 9.028±0.2, 11.196±0.2, 12.200±0.2, 15.406±0.2, 16.380±0.2, 16.828±0.2, 17.393±0.2, 18.066±0.2, 18.739±0.2, 20.036±0.2, 20.894±0.2, 22.504±0.2, 22.955±0.2, 24.973±0.2, 25.505±0.2, 26.312±0.2, 26.918±0.2, 27.556±0.2, 28.403±0.2, 29.176±0.2, 31.586±0.2, 35.168±0.2.

Preferably, Crystal Form I has an X-ray powder diffraction pattern obtained by using Cu-Kα radiation substantially as shown in FIG. 1.

The present invention further provides a method A for preparing Crystal Form I of Compound 1 hydrochloride monohydrate, comprising:

1) dissolving Compound 1 hydrochloride in water;
2) adding sodium chloride to the solution of step 1); and
3) cooling down, crystallizing, filtering, and drying to give Crystal Form I.

According to the present invention, the followings are preferred.

In step 1), water may be heated before or after the addition of Compound 1 hydrochloride to dissolve Compound 1 hydrochloride; wherein water may be used in an amount 2-80 times, for example, 4-70 times, 6-60 times, 8-50 times, or 10-25 times, the weight of Compound 1 hydrochloride; and water may be heated to, for example, 70-100° C., such as 75° C., 80° C., 85° C., 90° C. or 95° C.

In step 2), sodium chloride may be added while maintaining the temperature of the solution of step 1). As an example, the amount of sodium chloride may be controlled so that it makes up 0.1-26%, for example, 0.5-20%, 0.8-15%, or 1-10%, for example, 3-5%, of the total weight of the solution.

Said sodium chloride may be in its suitable form, for example, a sodium chloride solution or sodium chloride solid can be used. Preferably, sodium chloride is added and then stirred to dissolve. The sodium chloride solution is preferably an aqueous solution of sodium chloride, wherein the weight percentage content of sodium chloride may be in the range from 10% to the saturated concentration, for example, 12%, 15%, 16%, 17%, 18%, 20%, 22%, 24%, 25%, or 26%.

In step 3), the mixture may be slowly cooled down to below 60° C. (e.g., 20 to 50° C.) under stirring to crystallize, followed by filtration by suction, rinsing, and drying in vacuo at 15-35° C. (e.g., 20° C., 25° C., or 30° C.), to give Crystal Form I of Compound 1 hydrochloride monohydrate.

The present invention also provides a method B for preparing Crystal Form I of Compound 1 hydrochloride monohydrate, comprising:

1) dissolving Compound 1 hydrochloride in an aqueous solution of ethanol; and
2) cooling down, crystallizing, filtering, and drying to give Crystal Form I.

According to the present invention, the followings are preferred.

In step 1), the aqueous solution of ethanol may be heated before or after the addition of Compound 1 hydrochloride to dissolve Compound 1 hydrochloride; wherein the amount of the aqueous solution of ethanol used may be 5-80 times, for example, 10-70 times, 20-60 times, or 30-50 times the weight of Compound 1 hydrochloride; the aqueous solution of ethanol may be heated to, for example, 50-100° C., e.g., 55° C., 60° C., 65° C., 70° C., 75° C., 80° C., 85° C., 90° C. or 95° C.

The mass percentage of ethanol in the aqueous solution of ethanol may be, for example, 30 to 99%, such as 40 to 98%, 45 to 95%, 46 to 85%, 48 to 80%, 50 to 75%, or 60 to 70%.

In step 2), the mixture may be slowly cooled down to below 40° C. (e.g., 20 to 30° C.) under stirring to crystallize, followed by filtration by suction, and drying in vacuo at 15 to 35° C. (e.g., room temperature, i.e. 25° C.) to give Crystal Form I of Compound 1 hydrochloride monohydrate.

The present invention also provides Crystal Form II of Compound 1 hydrochloride monohydrate, which is characterized by an X-ray powder diffraction pattern obtained by using Cu-Kα radiation which may comprise characteristic peaks expressed in 2-theta angle (°) at 8.934±0.2, 11.126±0.2, 15.367±0.2, 22.437±0.2.

According to the present invention, the X-ray powder diffraction pattern of Crystal Form II obtained by using Cu-Kα radiation comprises characteristic peaks expressed in 2-theta angle (°) at 8.934±0.2, 11.126±0.2, 12.161±0.2, 15.367±0.2, 16.289±0.2, 17.369±0.2, 18.037±0.2, 18.667±0.2, 20.896±0.2, 22.437±0.2, 22.928±0.2, 24.995±0.2, 26.269±0.2, 26.890±0.2, 27.574±0.2.

Preferably, the X-ray powder diffraction pattern of Crystal Form II obtained by using Cu-Kα radiation comprises characteristic peaks expressed in 2-theta angle (°) at 8.486±0.2, 8.934±0.2, 11.126±0.2, 12.161±0.2, 13.317±0.2 15.367±0.2, 16.289±0.2, 16.742±0.2, 17.369±0.2, 18.037±0.2, 18.667±0.2, 19.966±0.2, 20.896±0.2, 22.437±0.2, 22.928±0.2, 24.995±0.2, 25.467±0.2, 26.269±0.2, 26.890±0.2, 27.213±0.2, 27.574±0.2, 28.366±0.2, 29.075±0.2, 35.001±0.2.

Preferably, Crystal Form II has an X-ray powder diffraction pattern obtained by using Cu-Kα radiation substantially as shown in FIG. 8.

The present invention also provides a method for preparing Crystal Form II of Compound 1 hydrochloride monohydrate, comprising:

1) mixing saturated solutions obtained by dissolving Compound 1 hydrochloride in two different solvents; and
2) evaporating solvents from the mixture of step 1) to give Crystal Form II.

According to the preparation method of the present invention, the followings are preferred.

In step 1), the two saturated solutions may be mixed at a temperature of 10 to 35° C., preferably 20 to 25° C. The solvent is selected from organic solvents, for example, one or more selected from the group consisting of ester solvents (such as ethyl acetate, methyl acetate, ethyl formate, methyl formate), ketone solvents (such as acetone, 2-butanone), ether solvents (such as tetrahydrofuran, 1,4-dioxane, methyl tert-butyl ether, methyl isopropyl ether, methyl ethyl ether, diethyl ether), nitrile solvents (such as acetonitrile, propionitrile). Preferably, the ratio of the respective total volumes of the two saturated solutions is from 2:1 to 1:2, for example 1:1. For example, the two saturated solutions may be mixed in a 96-well plate.

In step 2), the mixture of step 1) may be placed in ambient atmosphere to slowly evaporate the solvents. As an example, the 96-well plate may be covered with a punctured sealing film, placed in a fume hood, and naturally dried in ambient atmosphere to give Crystal Form II.

The present invention also provides Crystal Form III of Compound 1 hydrochloride, which is characterized by an X-ray powder diffraction pattern obtained by using Cu-Kα radiation which may comprise characteristic peaks expressed in 2-theta angle (°) at 6.396±0.2, 7.115±0.2, 8.972±0.2, 10.803±0.2, 11.870±0.2, 18.542±0.2, 23.071±0.2.

According to the present invention, the X-ray powder diffraction pattern of Crystal Form III may comprise characteristic peaks expressed in 2-theta angle (°) at 6.396±0.2, 7.115±0.2, 8.972±0.2, 10.803±0.2, 11.147±0.2, 11.870±0.2, 12.139±0.2, 15.417±0.2, 16.297±0.2, 16.559±0.2, 17.374±0.2, 18.074±0.2, 18.542±0.2, 19.310±0.2, 22.464±0.2, 23.071±0.2, 24.550±0.2, 25.843±0.2, 26.903±0.2, 28.737±0.2, 29.664±0.2, 35.016±0.2.

Preferably, Crystal Form III has an X-ray powder diffraction pattern obtained by using Cu-Kα radiation substantially as shown in FIG. 10.

The present invention also provides a method for preparing Crystal Form III of Compound 1 hydrochloride monohydrate, comprising:

1) mixing saturated solutions obtained by dissolving Compound 1 hydrochloride in two different solvents; and 2) evaporating solvents from the mixture of step 1) to give Crystal Form III.

According to the preparation method of the present invention, the followings are preferred.

In step 1), the two saturated solutions may be mixed at a temperature below 35° C., preferably 20 to 25° C. The solvent is selected from organic solvents, for example, one or more selected from the group consisting of alcohol solvents (such as methanol, ethanol, n-propanol, iso-propanol, n-butanol), ether solvents (such as tetrahydrofuran, 1,4-dioxane, methyl tert-butyl ether, methyl isopropyl ether, methyl ethyl ether, diethyl ether). Preferably, the ratio of the respective total volumes of the two saturated solutions is from 2:1 to 1:2, for example 1:1. For example, the two saturated solutions may be mixed in a 96-well plate.

In step 2), the mixture of step 1) may be placed in ambient atmosphere to slowly evaporate the solvents. As an example, the 96-well plate may be covered with a punctured sealing film, placed in a fume hood, and naturally dried in ambient atmosphere to give Crystal Form III.

The present invention also provides Crystal Form IV of Compound 1 hydrochloride, which is characterized by an X-ray powder diffraction pattern obtained by using Cu-Kα radiation which may comprise characteristic peaks expressed in 2-theta angle (°) at 6.178±0.2, 8.996±0.2, 11.170±0.2, 15.393±0.2, 16.343±0.2, 17.349±0.2, 18.064±0.2, 18.708±0.2, 19.479±0.2, 19.994±0.2, 20.901±0.2, 22.470±0.2, 22.935±0.2, 24.964±0.2, 25.504±0.2, 26.287±0.2, 26.920±0.2, 27.545±0.2.

According to the present invention, the X-ray powder diffraction pattern of Crystal Form IV obtained by using Cu-Kα radiation may comprise characteristic peaks expressed in 2-theta angle (°) at 6.178±0.2, 6.614±0.2, 7.181±0.2, 7.470±0.2, 8.996±0.2, 11.170±0.2, 11.723±0.2, 12.183±0.2, 13.323±0.2, 14.412±0.2, 15.393±0.2, 16.343±0.2, 16.777±0.2, 17.349±0.2, 18.064±0.2, 18.708±0.2, 19.479±0.2, 19.994±0.2, 20.901±0.2, 22.470±0.2, 22.935±0.2, 24.964±0.2, 25.504±0.2, 26.287±0.2, 26.920±0.2, 27.545±0.2, 28.363±0.2, 28.841±0.2, 29.152±0.2, 31.487±0.2, 33.970±0.2, 35.136±0.2.

Preferably, Crystal Form IV has an X-ray powder diffraction pattern obtained by using Cu-Kα radiation substantially as shown in FIG. 11.

The present invention also provides a method for preparing Crystal Form IV of Compound 1 hydrochloride monohydrate, comprising:

1) mixing saturated solutions obtained by dissolving Compound 1 hydrochloride in two different solvents; and 2) evaporating solvents from the mixture of step 1) to give Crystal Form IV.

According to the preparation method of the present invention, the followings are preferred.

In step 1), the two saturated solutions may be mixed at a temperature below 35° C., preferably 20 to 25° C. The solvent is selected from organic solvents, for example, one or more selected from the group consisting of aromatic hydrocarbon solvents (such as benzene, toluene, xylene, and chlorobenzene), ester solvents (such as ethyl acetate, methyl acetate, ethyl formate, methyl formate). Preferably, the ratio of the respective total volumes of the two saturated solutions is 2:1 to 1:2, for example 1:1. For example, the two saturated solutions may be mixed in a 96-well plate.

In step 2), the mixture of step 1) may be placed in ambient atmosphere to slowly evaporate the solvents. As an example, the 96-well plate may be covered with a punctured sealing film, placed in a fume hood, and naturally dried in ambient atmosphere to give Crystal Form IV.

The present invention also provides Crystal Form V of Compound 1 hydrochloride dihydrate, which is characterized by an X-ray powder diffraction pattern obtained by using Cu-Kα radiation which may comprise characteristic peaks expressed in 2-theta angle (°) at 6.181±0.2, 8.318±0.2, 18.223±0.2, 31.778±0.2.

According to the present invention, the X-ray powder diffraction pattern of Crystal Form V obtained by using Cu-Kα radiation may comprise characteristic peaks expressed in 2-theta angle (°) at 6.181±0.2, 7.226±0.2, 8.318±0.2, 9.524±0.2, 10.496±0.2, 12.037±0.2, 18.223±0.2, 27.421±0.2, 31.778±0.2.

Preferably, Crystal Form V has an X-ray powder diffraction pattern obtained by using Cu-Kα radiation substantially as shown in FIG. 13.

The present invention also provides a method for preparing Crystal Form V of Compound 1 hydrochloride dihydrate, comprising:

1) preparing a saturated solution of Compound 1 hydrochloride in saline; and 2) allowing the solution of step 1) to stand, crystallizing, and filtering by suction to give Crystal Form V.

According to the preparation method of the present invention, the followings are preferred.

In step 1), the saturated solution of Compound 1 hydrochloride in saline is a saturated solution of Compound 1 hydrochloride in an aqueous solution of sodium chloride. The weight percentage of sodium chloride in the saturated solution may be from 1% to saturated concentration, for example, 1%, 5%, 10%, 12%, 15%, 16%, 17%, 18%, 20%, 22%, 24%, 25%, or 26%.

Preferably, the saturated solution of step 1) is derived from the mother liquor after filtration in step 3) of the above-mentioned method A for preparing Crystal Form I.

In step 2), the solution may be allowed to stand for above 8 hours, e.g., overnight, or above 24 hours, e.g., above 36 hours, above 48 hours, or above seven days at a temperature below 40° C., for example, below 30° C., such as 20-25° C.

The present invention also provides Crystal Form VI of Compound 1 hydrochloride dihydrate, which is characterized by an X-ray powder diffraction pattern obtained by using Cu-Kα radiation which may comprise characteristic peaks expressed in 2-theta angle (°) at 7.489±0.2, 8.897±0.2, 11.140±0.2, 11.638±0.2, 13.348±0.2, 13.755±0.2, 16.110±0.2, 17.152±0.2, 18.782±0.2, 19.865±0.2, 20.891±0.2, 21.477±0.2, 25.245±0.2, 26.184±0.2, 26.431±0.2, 27.242±0.2, 28.489±0.2.

According to the present invention, the X-ray powder diffraction pattern of Crystal Form VI obtained by using Cu-Kα radiation may comprise characteristic peaks expressed in 2-theta angle (°) at 7.489±0.2, 8.153±0.2, 8.897±0.2, 11.140±0.2, 11.638±0.2, 13.348±0.2, 13.755±0.2, 14.985±0.2, 15.467±0.2, 16.110±0.2, 17.152±0.2, 18.240±0.2, 18.782±0.2, 19.865±0.2, 20.891±0.2, 21.477±0.2, 22.333±0.2, 22.888±0.2, 25.245±0.2, 26.184±0.2, 26.431±0.2, 27.242±0.2, 28.489±0.2, 29.710±0.2.

Preferably, Crystal Form VI has an X-ray powder diffraction pattern obtained by using Cu-Kα radiation substantially as shown in FIG. 15.

The present invention also provides a method for preparing Crystal Form VI of Compound 1 hydrochloride dihydrate, comprising:
1) dissolving Compound 1 hydrochloride in a mixture of water and acetonitrile; and
2) stirring, crystallizing, filtering, and drying, to give Crystal Form VI.

According to the present invention, the followings are preferred.

In step 1), Compound 1 hydrochloride may be dissolved in the mixture of water and acetonitrile at a temperature below 40° C., e.g., below 30° C., such as 20-25° C. The volume percentage of acetonitrile in the mixture of water and acetonitrile may be, for example, 5 to 99%, such as 10 to 95%, 15 to 75%, 20 to 60%, or 25 to 50%.

In step 2), the stirring may be performed for 20 hours at a temperature below 40° C., e.g., below 30° C., e.g., 20 to 25° C., where a large amount of white crystal is precipitated, which is filtered by suction. The resulting solid may be dried in vacuo at 25° C. to give Crystal Form VI.

The present invention also provides Crystal Form VII of Compound 1 hydrochloride dihydrate, which is characterized by an X-ray powder diffraction pattern obtained by using Cu-Kα radiation which may comprise characteristic peaks expressed in 2-theta angle (°) at 6.264±0.2, 6.760±0.2, 7.556±0.2, 14.455±0.2, 20.123±0.2, 26.373±0.2.

According to the present invention, the X-ray powder diffraction pattern of Crystal Form VII obtained by using Cu-Kα radiation may comprise characteristic peaks expressed in 2-theta angle (°) at 6.264±0.2, 6.760±0.2, 7.556±0.2, 11.414±0.2, 11.743±0.2, 12.488±0.2, 13.419±0.2, 14.455±0.2, 17.246±0.2, 18.099±0.2, 20.123±0.2, 21.082±0.2, 25.370±0.2, 26.373±0.2, 27.294±0.2.

Preferably, Crystal Form VII has an X-ray powder diffraction pattern obtained by using Cu-Kα radiation substantially as shown in FIG. 17.

The present invention also provides a method A for preparing Crystal Form VII of Compound 1 hydrochloride dihydrate, comprising:

1) dissolving Compound 1 hydrochloride in water;
2a) cooling the aqueous solution of step 1) to crystallize; or 2b) adding sodium chloride to the aqueous solution of step 1) and stirring to crystallize; and
3) filtering, and drying, to give Crystal Form VII.

According to the method of the present invention, the followings are preferred.

In step 1), the amount of water used is 10 to 500 times, for example, 20 to 200 times, such as 60 or 180 times, the weight of Compound 1 hydrochloride. Preferably, water is heated before or after Compound 1 hydrochloride is added. Preferably, a step of hot filtration to remove insolubles is also included. Water may be heated to 70-100° C., such as 75° C., 80° C., 85° C., 90° C. or 95° C.

In step 2a), the aqueous solution of step 1) is cooled down to below 40° C., for example, below 30° C., such as at 20-25° C., to crystallize.

In step 2b), the solution is stirred at below 40° C., for example, below 30° C., such as 20 to 25° C., to crystallize. Sodium chloride may be in a suitable form thereof, for example, a sodium chloride solution or sodium chloride solid may be used. Preferably, sodium chloride is added and then dissolved by stirring. For example, the amount of sodium chloride used may be 1 to 15 times, for example, 4 to 8 times, that of Compound 1 hydrochloride.

Steps 2a) and 2b) are performed alternatively.

In step 3), the filtering may be filtering by suction, and the drying may be drying in vacuo.

The present invention also provides a method B for preparing Crystal Form VII of Compound 1 hydrochloride dihydrate, comprising:

mixing and beating one or more of the above-mentioned Crystal Forms I-VI with water for 3 days to give Crystal Form VII.

Preferably, the mixing and beating in the method are performed at below 40° C., for example, below 30° C., such as 20-25° C. The amount of water used in the mixing and beating is 20 to 200 times, for example, 100 times, the total weight of Crystal Forms I-VI.

The present invention also provides a pharmaceutical composition comprising one or more of the above-mentioned crystals or crystal forms.

According to the present invention, the pharmaceutical composition may further comprise a pharmaceutically acceptable carrier.

The pharmaceutically acceptable carrier is preferably a carrier that is relatively non-toxic and harmless to the patient at a concentration that is consistent with the effective activity of the active ingredient so that any side effects caused by the carrier do not destroy the beneficial effects of the active ingredient. The pharmaceutically effective amount of the compound or pharmaceutically acceptable salt thereof is preferably an amount that produces a result or exerts an influence on the particular condition being treated. The compound of the present invention may be administered in any effective conventional dosage unit form, including immediate release, sustained release, and timed release formulations, with pharmaceutically acceptable carriers well known in the art by routes such as oral, parenteral, topical, nasal, ocular, sublingual, rectal, vaginal, etc.

For oral administration, the compound or a pharmaceutically acceptable salt thereof may be formulated into a solid or liquid preparation such as capsule, pill, tablet, troche, lozenge, melt, powder, solution, suspension or emulsion, which may be prepared according to methods known in the art for preparing pharmaceutical compositions. The solid unit dosage form may be a capsule, which may be of the ordinary hard-capsule or soft-capsule type, containing, for example, surfactant, lubricant, and inert filler (such as lactose, sucrose, calcium phosphate, and corn starch).

In another embodiment, the compound of the present invention, or a pharmaceutically acceptable salt thereof, may be tableted together with a conventional tablet base (e.g., lactose, sucrose, and corn starch) and in combination with an adhesive (for example, gum arabic, corn starch, or gelatin), a disintegrant for facilitating the breakdown and dissolution of the tablet after administration (e.g., potato starch, alginic acid, corn starch, and guar gum, gum tragacanth, gum arabic), a lubricant for increasing the flowability of the tablet granulation and preventing the surface adhesion of the tablet material to the tablet mold and the head punch (e.g., talc, stearic acid or magnesium stearate, calcium stearate or zinc stearate), a dye, a colorant, and a flavoring agent for improving the sensory properties of the tablet and making it more acceptable to the patient (e.g., peppermint oil, wintergreen oil, or cherry essence). Suitable excipients for oral liquid dosage forms include dicalcium phosphate and diluents such as water and alcohol (e.g., ethanol, benzyl alcohol and polyvinyl alcohol) with or without the addition of a pharmaceutically acceptable surfactant, suspending agent or emulsifier. Various other substances may be present as a coating or for changing the physical form of the dosage unit. For example, the tablet, pill or capsule may be coated with shellac, sugar or both.

The compound of the present invention may also be parenterally, i.e. subcutaneously, intravenously, intraocularly, intrasynovially, intramuscularly or intraperitoneally, administered as an injection of the compound, and the injection is preferably in a physiologically acceptable diluent containing a pharmaceutical carrier. The pharmaceutical carrier may be a sterile liquid or a mixture of liquids, such as water, saline, aqueous solution of glucose and relevant sugar solutions, an alcohol such as ethanol, isopropanol or cetyl alcohol, a diol such as propylene glycol or polyethylene glycol, a glycerol ketal such as 2,2-dimethyl-1,1-dioxolane-4-methanol, an ether such as polyethylene glycol 400 (PEG 400), an oil, a fatty acid, a fatty acid ester or fatty acid glyceride or acetylated fatty acid glyceride. The diluent is added or not added with a pharmaceutically acceptable surfactant such as soap or detergent, a suspending agent such as pectin, carbomer, and methylcellulose, hydroxypropyl methylcellulose or carboxymethylcellulose, or an emulsifier and other pharmaceutical auxiliaries.

Exemplary surfactants for parenteral formulations are polyethylene sorbitan fatty acid esters, such as sorbitan monooleate, and high molecular weight adducts of ethylene oxide with a hydrophobic matrix, wherein the hydrophobic matrix is formed by condensation of propylene oxide and propylene glycol.

The composition of the present invention may also be administered in the form of a suppository for rectal administration of the drug. This composition may be prepared by mixing the drug with a suitable non-irritating excipient that is solid at ambient temperature but liquid at rectal temperature and therefore can be dissolved in the rectum to release the drug. Such materials are, for example, cocoa butter and polyethylene glycol.

Controlled release formulations for parenteral administration include liposomal microspheres, polymeric microspheres, and polymeric gel formulations known in the art.

A mechanical delivery device may or must be used to deliver the pharmaceutical composition to the patient. The construction and use of the mechanical delivery device for delivering a medicament are well known in the art. Direct techniques for direct administration of drugs, for example, to the brain typically involve placing a drug delivery catheter into the patient's cerebral ventricle system to bypass the blood-brain barrier.

The compound of the present invention may be administered as a single agent or in combination with one or more other agents wherein the combination does not cause an unacceptable adverse reaction. The present invention also relates to such combinations. For example, the compound of the present invention may be combined with known chemotherapeutic agents or anti-cancer agents (e.g., agents for anti-hyperproliferative diseases or other indications, etc.) as well as mixtures and combinations thereof. The agents for other indications include but are not limited to anti-angiogenesis agents, mitotic inhibitors, alkylating agents, antimetabolites, DNA-embedded antibiotics, growth factor inhibitors, cell cycle inhibitors, enzyme inhibitors, topoisomerase inhibitors, biological response modifiers or anti-hormones.

The present invention also provides one or more of the said crystal forms for the treatment or prevention of a disease associated with the activity of a protein kinase.

The present invention also provides a method for regulating (e.g., down-regulating) the activity of a protein kinase, comprising contacting the protein kinase with an effective amount of one or more of the crystal forms described above. The method may be used in vivo, and may be also used in vitro. Preferably, the protein kinase is at least one selected from the group consisting of mTOR and PI3K.

According to another aspect of the present application, the present application provides a method for treating a disease associated with the activity of a protein kinase, comprising administrating an effective amount of one or more of the crystal forms described above to an individual in need thereof. The individual may be a mammal, such as human.

The disease associated with the activity of a protein kinase according to the specification (e.g., the disease treated or prevented by inhibiting one or both of mTOR and PI3K kinases) may be a tumor, for example, leukemia, malignant lymphoma, multiple myeloma, gastrointestinal stromal tumor, colon cancer, rectal cancer, breast cancer, liver cancer, stomach cancer, ovarian cancer, uterine cancer, cervical cancer, vaginal cancer, choriocarcinoma, lung cancer, kidney cancer, prostate cancer, bladder cancer, pancreatic cancer, glioblastoma, mast cell tumor, cerebroma, germ cell tumor, melanoma, or sarcoma, including dermatofibrosarcoma protuberans and osteosarcoma. The disease associated with the activity of a protein kinase described in the present application may also be a metabolic disease (e.g., diabetes mellitus, obesity) and a cardiovascular disease (e.g., atherosclerosis).

The present invention also provides use of one or more of the crystal forms described above in the manufacture of a medicament for treating or preventing a disease or condition, which may be a disease or condition associated with the activity of a protein kinase, for example, including a disease that may be treated or prevented by inhibiting one or both of mTOR and PI3K kinases.

The present invention also provides use of one or more of the crystal forms described above in the manufacture of a medicament for inhibiting one or both of mTOR and PI3K kinases.

The said disease includes diseases caused by uncontrolled cell growth, proliferation and/or survival, inappropriate cellular immune responses or inappropriate cellular inflammatory responses, or is accompanied by diseases caused by uncontrolled cell growth, proliferation and/or survival, an inappropriate cellular immune response, or an inappropriate cellular inflammatory response. Particularly, the disease is, for example, a neoplastic hematologic disorder, a solid tumor, and/or their metastases, such as leukemia and myelodysplastic syndrome, malignant lymphoma, head and neck tumor including brain tumor and brain metastases, chest tumor including non-small cell lung tumor and small cell lung tumor, gastrointestinal tumor, endocrine tumor, breast tumor and other gynecological tumor, urinary system tumor including kidney tumor, bladder tumor and prostate carcinoma, skin tumor and sarcoma, and/or their metastases.

The present invention also provides use of the compound of the present invention and a composition thereof in the manufacture of a medicament for the treatment of a hyperproliferative disorder in a mammal. The compound may be used to inhibit, block, decrease, reduce, etc. cell proliferation and/or cell division and/or cause apoptosis. The hyperproliferative disorder includes, but is not limited to, psoriasis, keloid and other hyperplasia affecting the skin, benign prostatic hyperplasia (BpH), solid tumor such as breast cancer, respiratory cancer, lung cancer, brain cancer, genital cancer, digestive tract cancer, urinary tract cancer, eye cancer, liver cancer, skin cancer, head and neck cancer, thyroid cancer, parathyroid cancer, and their distant metastases. The disorder also includes lymphoma, sarcoma and leukemia.

The term "metabolic disease" as used herein refers to a disease caused by metabolic problems including dysbolismus, exuberant metabolism, and others, and mainly includes the following diseases: diabetes mellitus, diabetic ketoacidosis, hyperglycosemia hyperosmolality syndrome, hypoglycemia, gout, protein-energy malnutrition, vitamin A deficiency, scurvy, vitamin D deficiency, osteoporosis, and the like.

The term "cardiovascular disease" as used herein is also known as circulatory disease, and is a series of diseases concerning the circulatory system. The circulatory system refers to organs and tissues carrying blood within the human body, mainly including heart, blood vessels (artery, vein, capillary). The cardiovascular disease can be subdivided into acute and chronic ones, both generally associated with arteriosclerosis. The cardiovascular disease includes heart diseases, hypotension, hypertension, hyperglycemia, stroke, myocardial infarction, thrombus, arteriosclerosis, and the like.

These disorders have been well characterized in humans, but are also present in other mammals with similar etiologies, and can be treated by administering the pharmaceutical composition of the present invention.

In some embodiments, the pharmaceutical composition may be in the form of tablet, capsule, pill, powder, sustained release preparation, solution or suspension for oral administration; sterile solution, suspension or emulsion for parenteral injection; ointment or cream for topical administration; or suppository for rectal administration. In further embodiments, the pharmaceutical composition is in a unit dosage form suitable for single administration of a precise dosage. In further embodiments, the amount of the compound is in a range of about 0.001 mg/kg body weight/day to about 1000 mg/kg body weight/day. In further embodiments, the amount of the compound is in a range of about 0.5 mg/kg body weight/day to about 50 mg/kg body weight/day. In some embodiments, the amount of the compound is about 0.001 g/day to about 7 g/day. In further embodiments, the amount of the compound is about 0.002 g/day to about 6 g/day. In further embodiments, the amount of the compound is about 0.005 g/day to about 5 g/day. In further embodiments, the amount of the compound is about 0.01 g/day to about 5 g/day. In further embodiments, the amount of the compound is about 0.02 g/day to about 5 g/day. In further embodiments, the amount of the compound is about 0.05 g/day to about 2.5 g/day. In further embodiments, the amount of the compound is about 0.1 g/day to about 1 g/day. In further embodiments, dosage levels below the lower limit of the aforesaid ranges may be adequate. In further embodiments, dosage levels above the upper limit of the aforesaid ranges may be required. In further embodiments, the compound is administered in a single dose once a day. In further embodiments, the compound is administered in multiple doses more than once a day. In further embodiments, the compound is administered twice a day. In further embodiments, the compound is administered three times a day. In further embodiments, the compound is administered four times a day. In further embodiments, the compound is administered more than four times a day. In some embodiments, the individual to which the pharmaceutical composition is administrated is a mammal. In further embodiments, the mammal is human. In further embodiments, the pharmaceutical composition further comprises at least one therapeutic agent (i.e., formulated into a single dosage form). In some embodiments, the pharmaceutical composition and the at least one therapeutic agent, respectively, in separate dosage forms, are combined into a combination product such as a kit of part.

The crystal forms provided in the present invention have good stabilities, including good stabilities under three extreme conditions, i.e. high temperature, high humidity and strong illumination, as well as good stabilities during the tableting process. The crystal forms provided in the present invention have good in vivo absorption and metabolism properties, including plasma drug concentration, time-concentration curve AUC, half-life, and the like. Moreover, the crystal forms of the present invention have improved the dissolution rate, which is advantageous to the application in the formulation.

Pharmaceutical Terminology

The relevant term "subject", "patient" or "individual" as used herein refers to an individual suffering from a disease, disorder or condition, and encompasses mammals and non-mammals. Examples of mammals include, but are not limited to, any member of the mammalian class: humans, non-human primates such as chimpanzees and other apes and monkeys; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fishes, and the like. In one embodiment of the method and composition provided herein, the mammal is a human.

The term "treat," "treating" or "treatment" as used herein and other similar synonyms includes alleviating, abating or ameliorating a symptom of a disease or condition, preventing other symptoms, ameliorating or preventing the underlying metabolic causes of a symptom, inhibiting a disease or condition, e.g., arresting the development of the disease or condition, relieving the disease or condition, causing improvement of the disease or condition, relieving a symptom caused by the disease or condition, or stopping a symptom of the disease or condition. In addition, the term encompasses a purpose of prophylaxis. The term further includes achieving a therapeutic benefit and/or a prophylactic benefit. By therapeutic benefit it is meant to eradicate or ameliorate the underlying disorder being treated. Furthermore, the eradication or amelioration of one or more physiological symptoms associated with the underlying disorder is also a therapeutic benefit; for example, an improvement is observed in the patient, notwithstanding that the patient may still be affected by the underlying disorder. For the prophylactic benefit, the composition may be administered to a patient at risk of developing a particular disease, or to a patient reporting one or more physiological symptoms of a disease, even though a diagnosis of this disease may not have been made.

The term "effective amount", "therapeutically effective amount" or "pharmaceutically effective amount" as used herein refers to a sufficient amount of at least one agent or compound being administered which will relieve to some extent one or more symptoms of the disease or condition being treated. The result can be reduction and/or alleviation of the signs, symptoms or causes of a disease, or any other desired alteration of a biological system. For example, an "effective amount" for therapeutic uses is the amount of the composition comprising a compound as disclosed herein required to provide a clinically significant alleviation of a disease. An effective amount suitable for any individual case may be determined using techniques such as a dose escalation study.

The term "administer", "administering", "administration", or the like, as used herein, refers to a method that may be used to deliver a compound or a composition to the desired site of biological action. These methods include, but are not limited to, oral route, transduodenal route, parenteral injection (including intravenous, subcutaneous, intraperitoneal, intramuscular, intra-arterial injection or infusion), topical and rectal administration. A person skilled in the art is familiar with the techniques for employing the compound and method described herein, e.g., those discussed in Goodman and Gilman, The Pharmacological Basis of Therapeutics, current ed.; Pergamon and Remington's, Pharmaceutical Sciences (current edition), Mack Publishing Co., Easton, Pa. In preferred embodiments, the compound and composition described herein are administered orally.

The term "acceptable" as used herein with respect to a formulation, composition or ingredient means having no persistent detrimental effect on the general health of the subject being treated.

DETAILED DESCRIPTION

Figure 1:
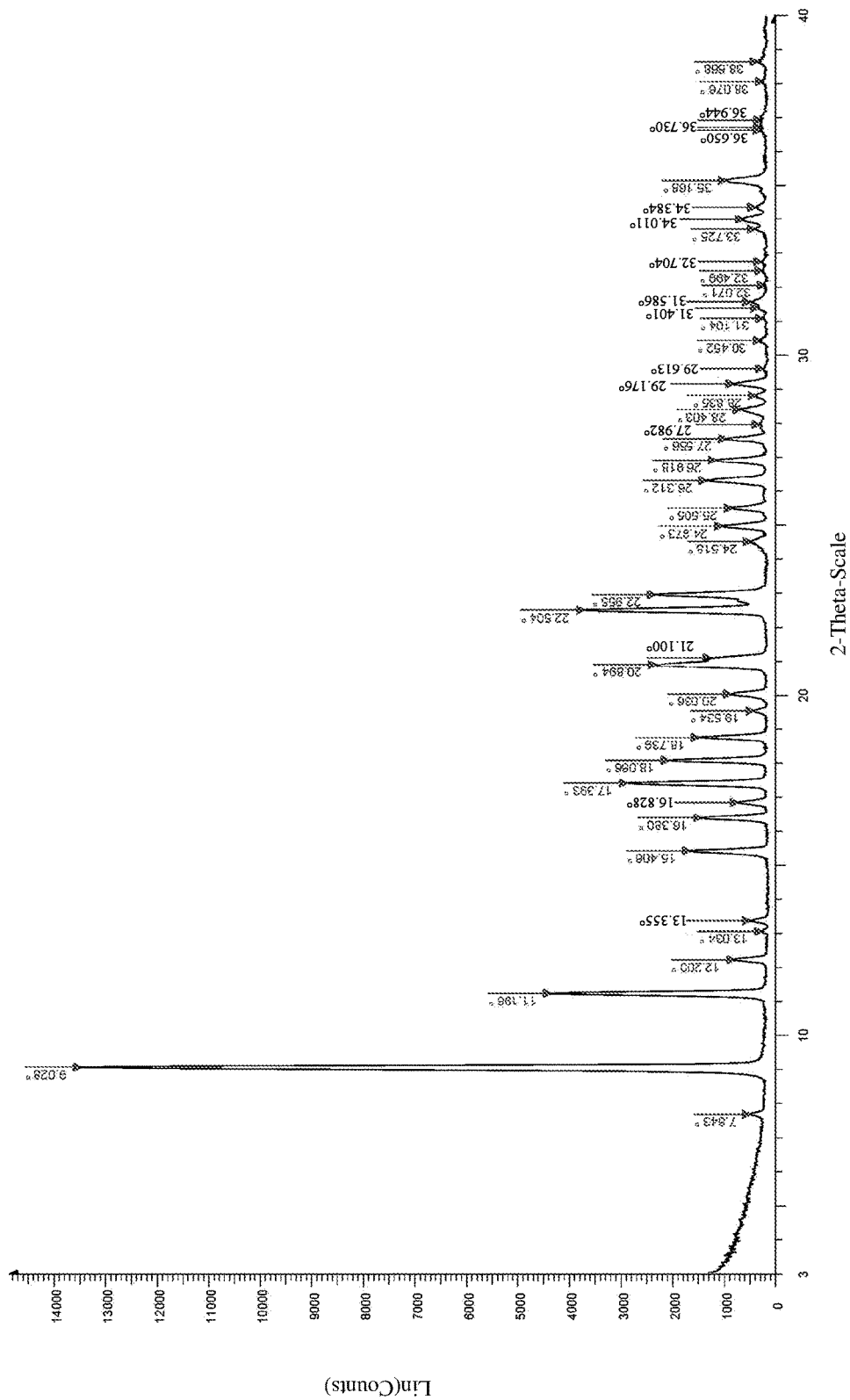
FIG. 1 is an X-ray powder diffraction (XRPD) pattern of Crystal Form I in Example I-1 obtained by using Cu-Kα radiation.
Figure 2:
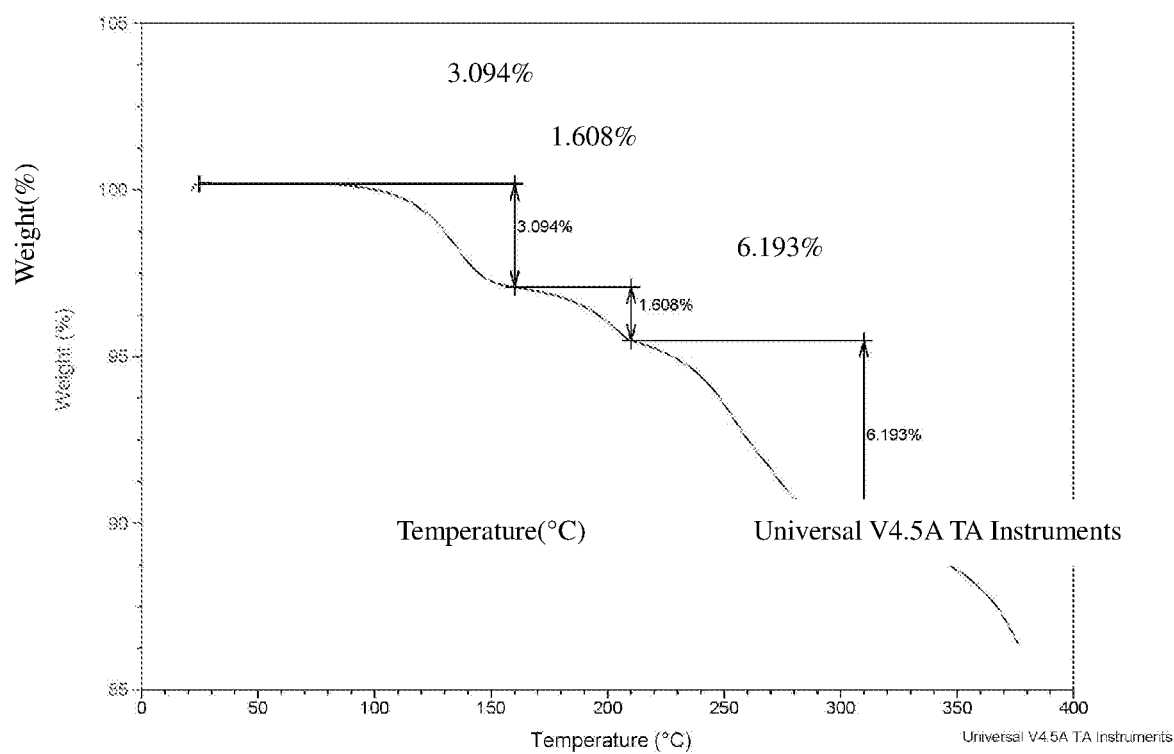
FIG. 2 is a thermogravimetric analysis (TGA) spectrum of Crystal Form I in Example I-1.
Figure 3:
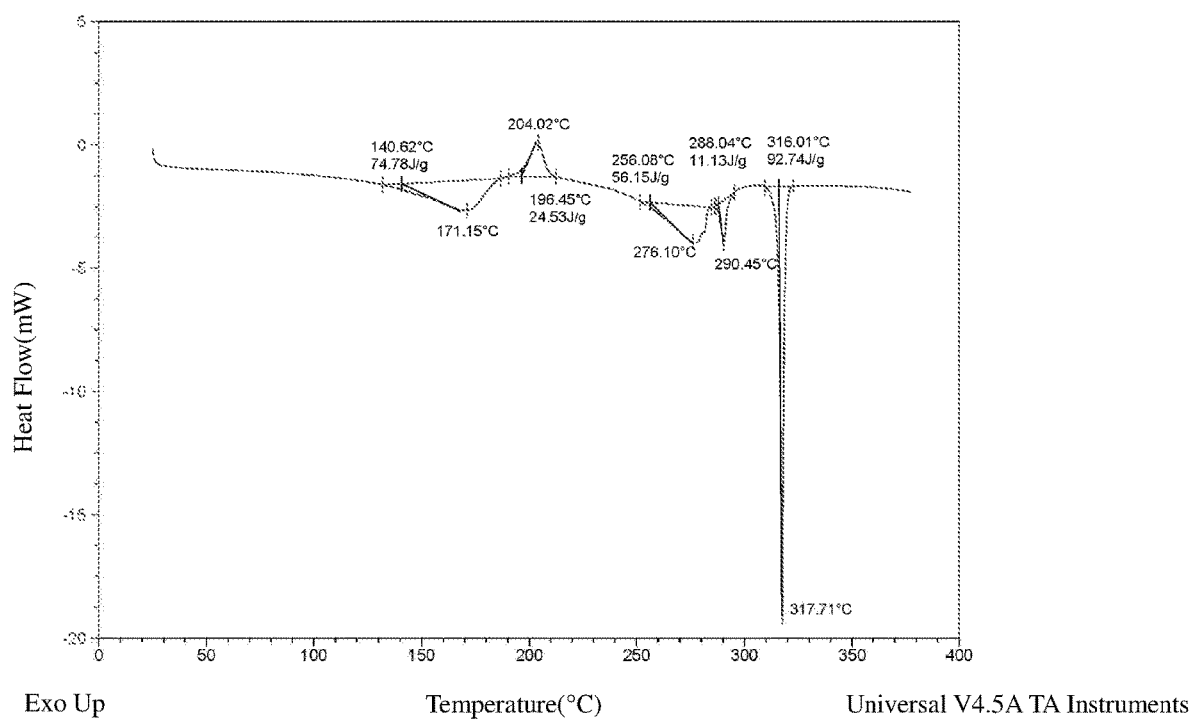
FIG. 3 is a differential scanning calorimetry (DSC) spectrum of Crystal Form I in Example I-1.

The technical solutions of the present invention will be described in detail through the following examples for better understanding of the technical solutions and essence of the present invention. The described examples are merely exemplary descriptions and should not be construed as limiting the scope of the present invention. Variations or changes made by a person skilled in the art based on the contents of the invention and the following examples are all covered in the scope of protection of the present invention.

The X-ray powder diffraction in the following examples was determined by a Bruker D8 advance type X-ray powder diffractometer equipped with a LynxEye detector. The 2-theta scan angle of the sample was from 3° to 40°, the scan step length was 0.02°, and the tube voltage and the tube current were 40 KV and 40 mA, respectively. The sample tray used for sample measurement is a zero background sample tray.

The differential scanning calorimetry (DSC) analysis in the following examples was performed using TA DSC Q200, the standard sample used for calibration was indium. 2-3 mg of sample was accurately weighed and placed on the TA DSC sample tray and the exact mass of the sample was recorded. The sample was heated to 200-250° C. at a heating rate of 10° C./min in 50 mL/min nitrogen stream. The thermogravimetric analysis in the following examples was performed using TA TGA Q500. 2-3 mg of sample was placed in a balanced aluminum sample tray and the sample mass was automatically measured in the TGA oven. The sample was heated to 200-300° C. at a rate of 10° C./min. During the test, nitrogen flow rates to the balance chamber and the sample chamber were 40 mL/min and 60 mL/min, respectively.

Unless otherwise indicated, the starting materials, substrates, or reagents in the following examples were all commercially available products (for example, the absolute ethanol used was commercially available analytically pure absolute ethanol), or were prepared by following the methods known in the art.

Example I-1: Preparation of Crystal Form I 96 g of Compound 1 hydrochloride was dissolved in 860 ml of water at a bath temperature of 100° C. 43 g of sodium chloride solid was added while the solution was still hot, and stirred to dissolve, followed by slowly cooling down to 30° C. to crystallize, filtering by suction, and rinsing with 100 ml of water. The resulting solid was dried in vacuo at 25° C. to give 86 g of yellow-green crystal that was characterized to be Crystal Form I of Compound 1 hydrochloride monohydrate.

Example I-2: Preparation of Crystal Form I 110 g of Compound 1 hydrochloride was dissolved in 2 liters of water at a bath temperature of 100° C. A solution of 100 g of sodium chloride in 500 ml of water was added while the solution was still hot, and the mixture was slowly cooled down to 20° C. under stirring to crystallize, filtered by suction, and rinsed with 100 ml of water. The resulting solid was dried in vacuo at 30° C. to give 97 g of yellow-green crystal that was characterized to be Crystal Form I of Compound 1 hydrochloride monohydrate.

Example I-3: Preparation of Crystal Form I 0.5 g of Compound 1 hydrochloride was dissolved in a mixture of 10 ml of ethanol and 5.5 ml of water at a bath temperature of 85° C. The mixture was naturally cooled down to 25° C. under stirring to crystallize, and filtered by suction. The resulting solid was dried in vacuo at 25° C. to give 0.36 g of yellow-green crystal that was characterized to be Crystal Form I of Compound 1 hydrochloride monohydrate.

Example I-4: Stability Test for Crystal Form I

A small amount of Crystal Form I of Compound 1 hydrochloride monohydrate of Example I-1 was taken and placed in a drug stability test box. The conditions were controlled as listed in Table 1 for the stability test. The results of the purities and the contents are listed in Table I-1, and the results of the crystal form tests are shown in FIGS. 4 to 6.

As shown in Table I-1, under three extreme conditions, i.e. high temperature, high humidity and strong illumination, the purity and the content of Crystal Form I of the compound do not change significantly (the fluctuation of the purity is within 0.2% and that of the content is within 1%), demonstrating that the stability of Crystal Form I is good.

Figure 4:
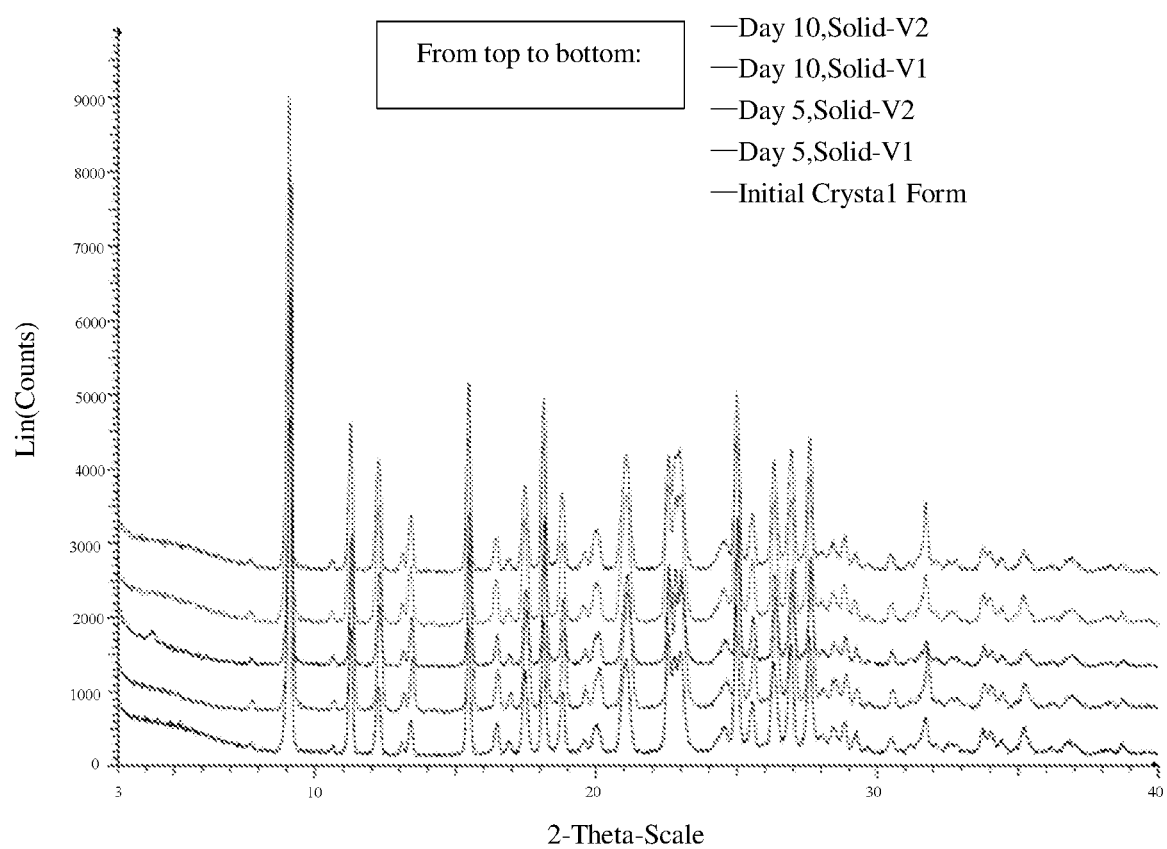
FIG. 4 is an XRPD pattern of the solid of Crystal Form I in Example I-4 at 60° C.
Figure 5:
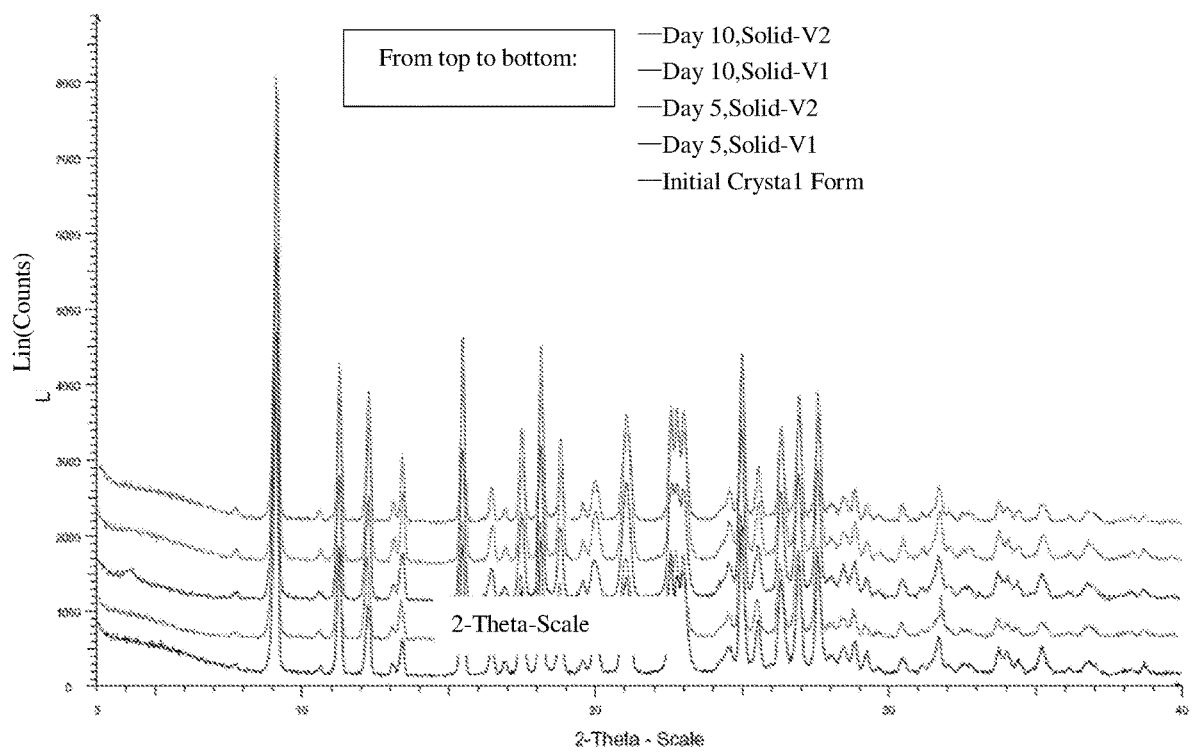
FIG. 5 is an XRPD pattern of the solid of Crystal Form I in Example I-4 at 25° C./90% RH.
Figure 6:
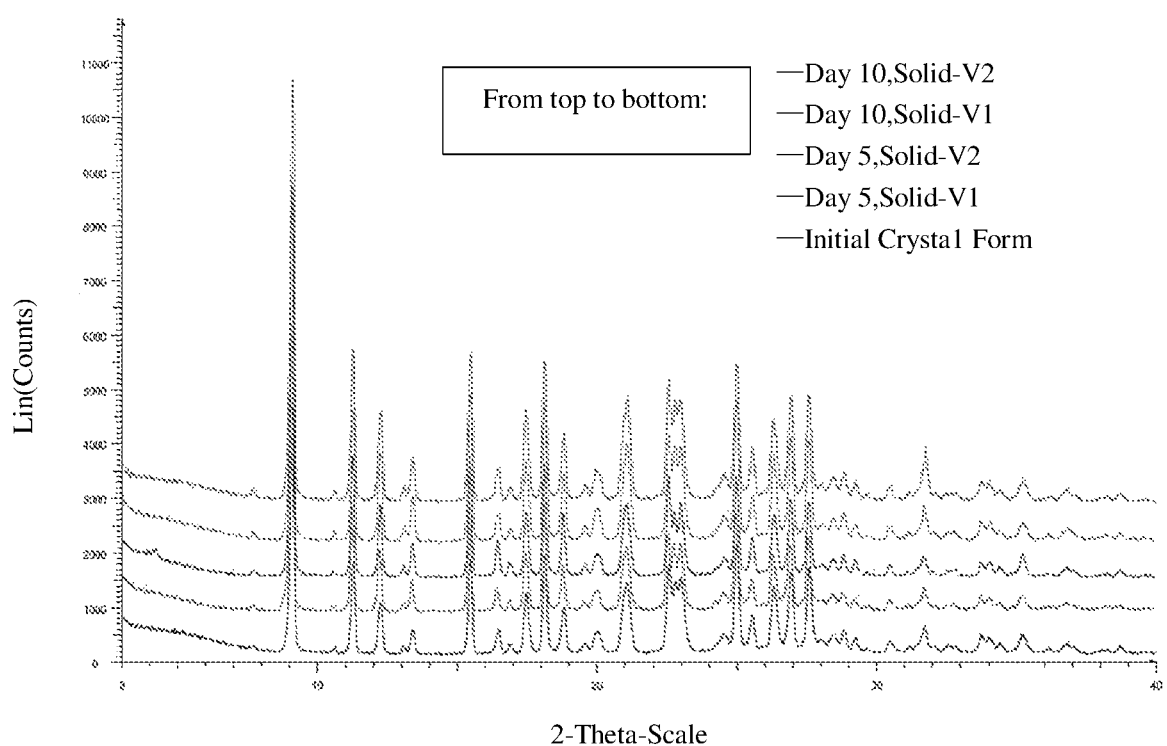
FIG. 6 is an XRPD pattern of the solid of Crystal Form I in Example I-4 under illumination.

As shown in FIGS. 4 to 6, under three extreme conditions, i.e. high temperature, high humidity and strong illumination, the crystal form of Crystal Form I remains unchanged, demonstrating that the stability of Crystal Form I is good.

TABLE I-1

Test Results of Solid Stability of Crystal Form I

| Conditions | Time | Purity % | Impurity % | Content % |
|---|---|---|---|---|
| Active Pharmaceutical Ingredient | Initial | 99.26 | 0.74 | 100.41 |
| 60° C. | Day 5 | 99.27 | 0.73 | 99.62 |
|  | Day 10 | 99.21 | 0.79 | 99.51 |
| 25° C./95% RH | Day 5 | 99.28 | 0.72 | 100.86 |
|  | Day 10 | 99.26 | 0.74 | 99.61 |
| Illumination (4500 Lx ± 500 Lx) | Day 5 | 99.07 | 0.93 | 99.84 |
|  | Day 10 | 99.13 | 0.87 | 99.50 |

Example I-5: Tableting Stability Test of Crystal Form I

Figure 7:
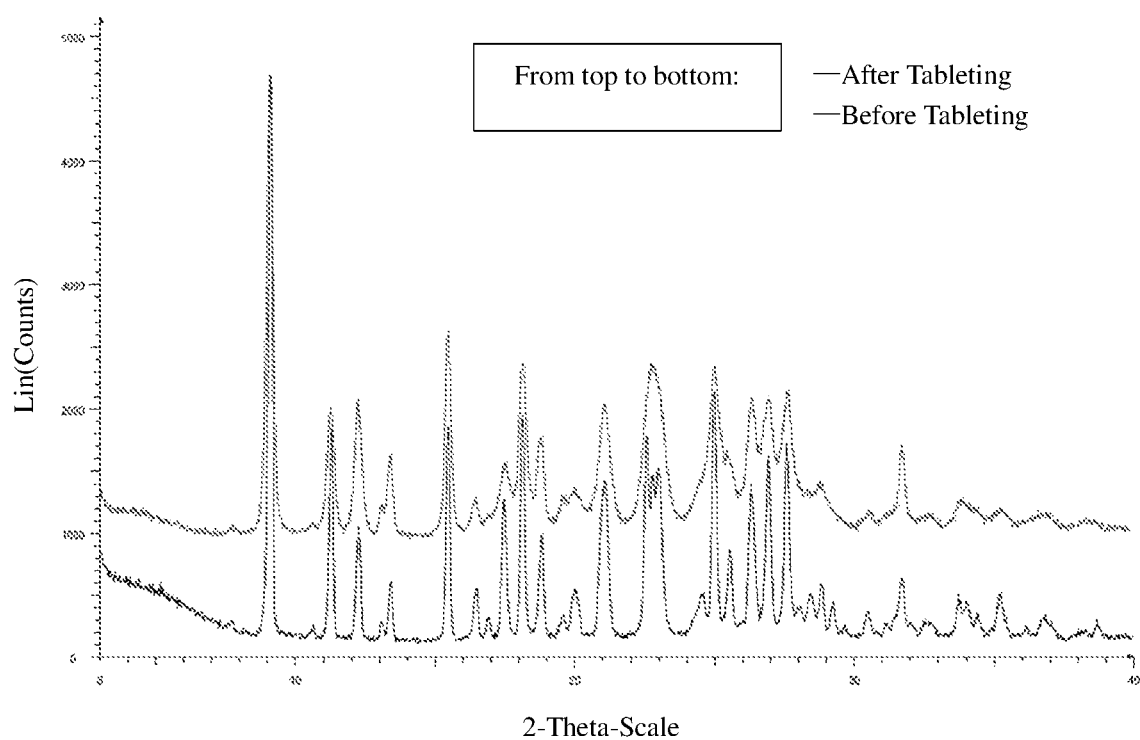
FIG. 7 is a comparison of the XRPD patterns before and after tableting of Crystal Form I in Example I-5.
Figure 8:
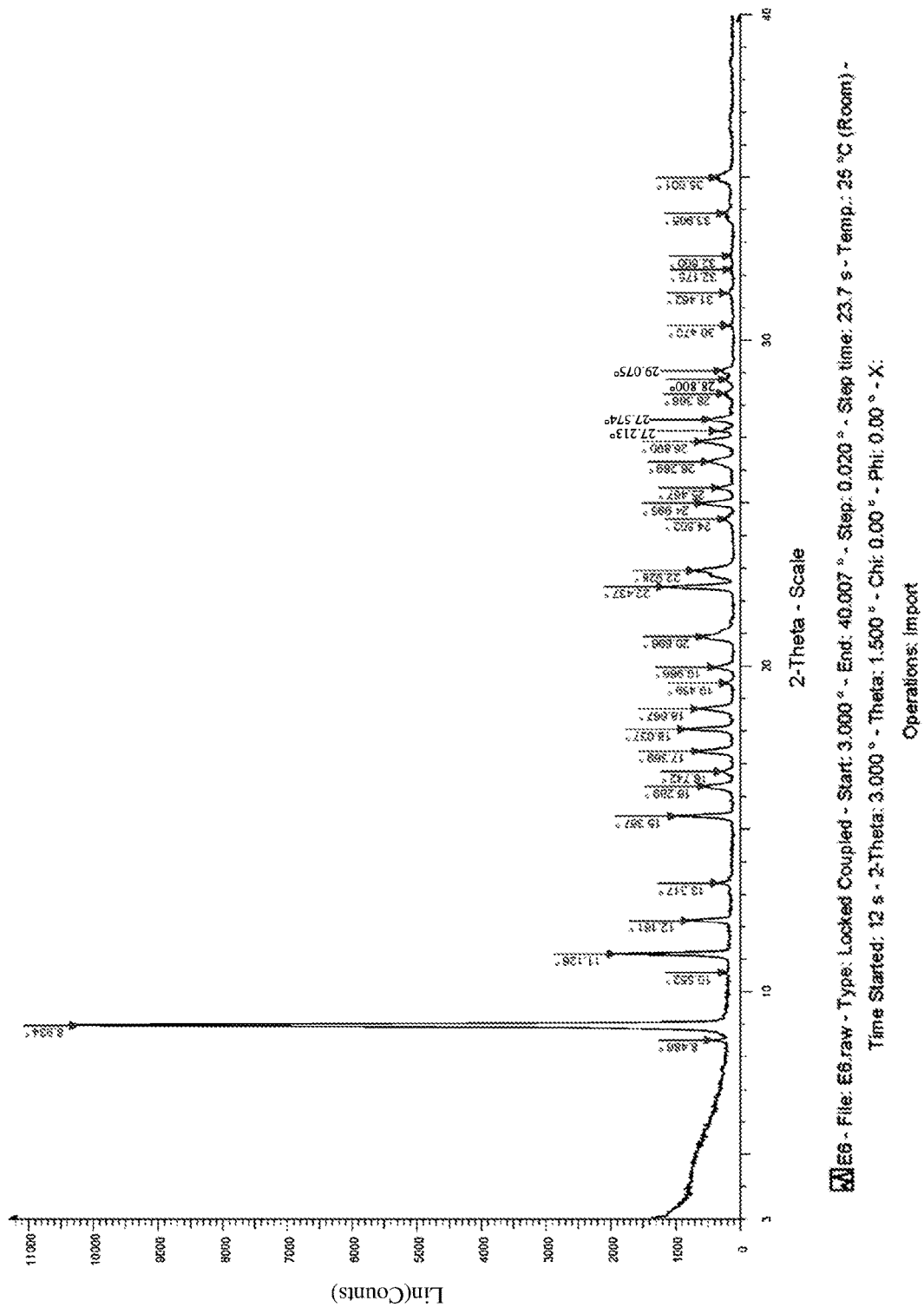
FIG. 8 is an XRPD pattern of Crystal Form II in Example II-1.
Figure 9:
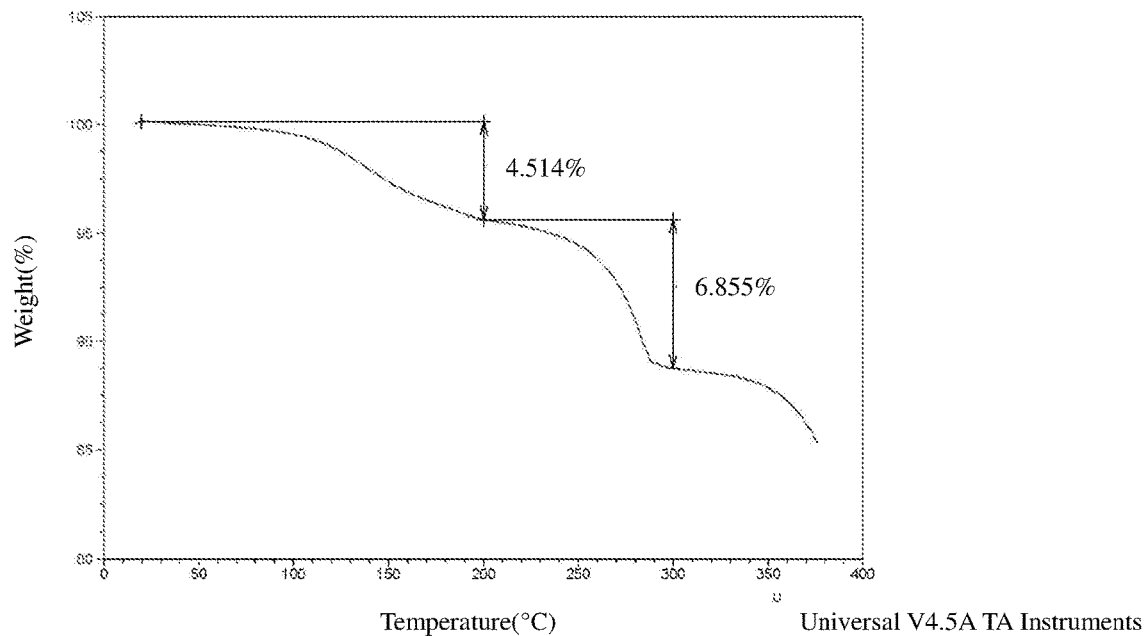
FIG. 9 is a TGA spectrum of Crystal Form II in Example II-1.
Figure 10:
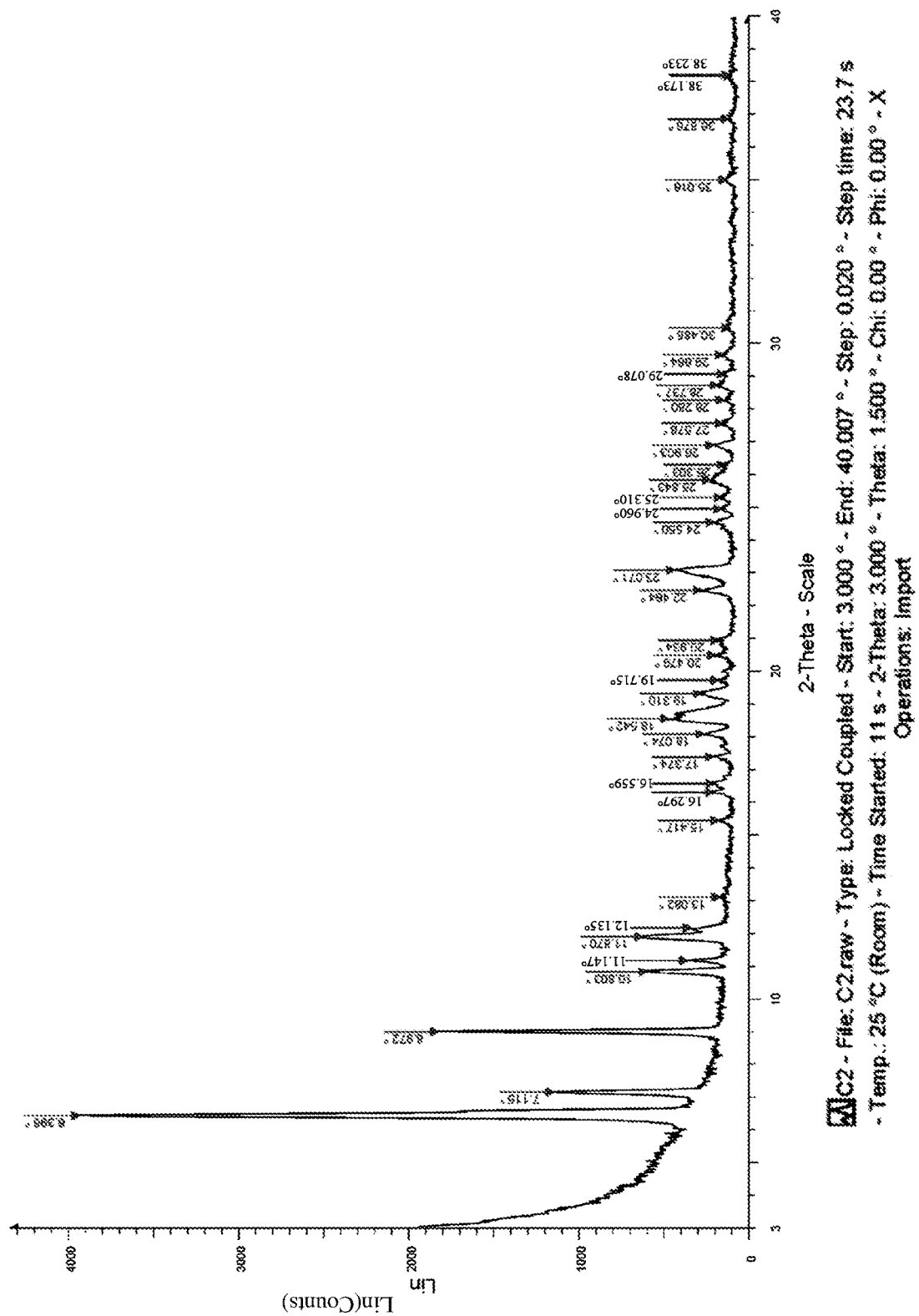
FIG. 10 is an XRPD pattern of Crystal Form III in Example III-1.
Figure 11:
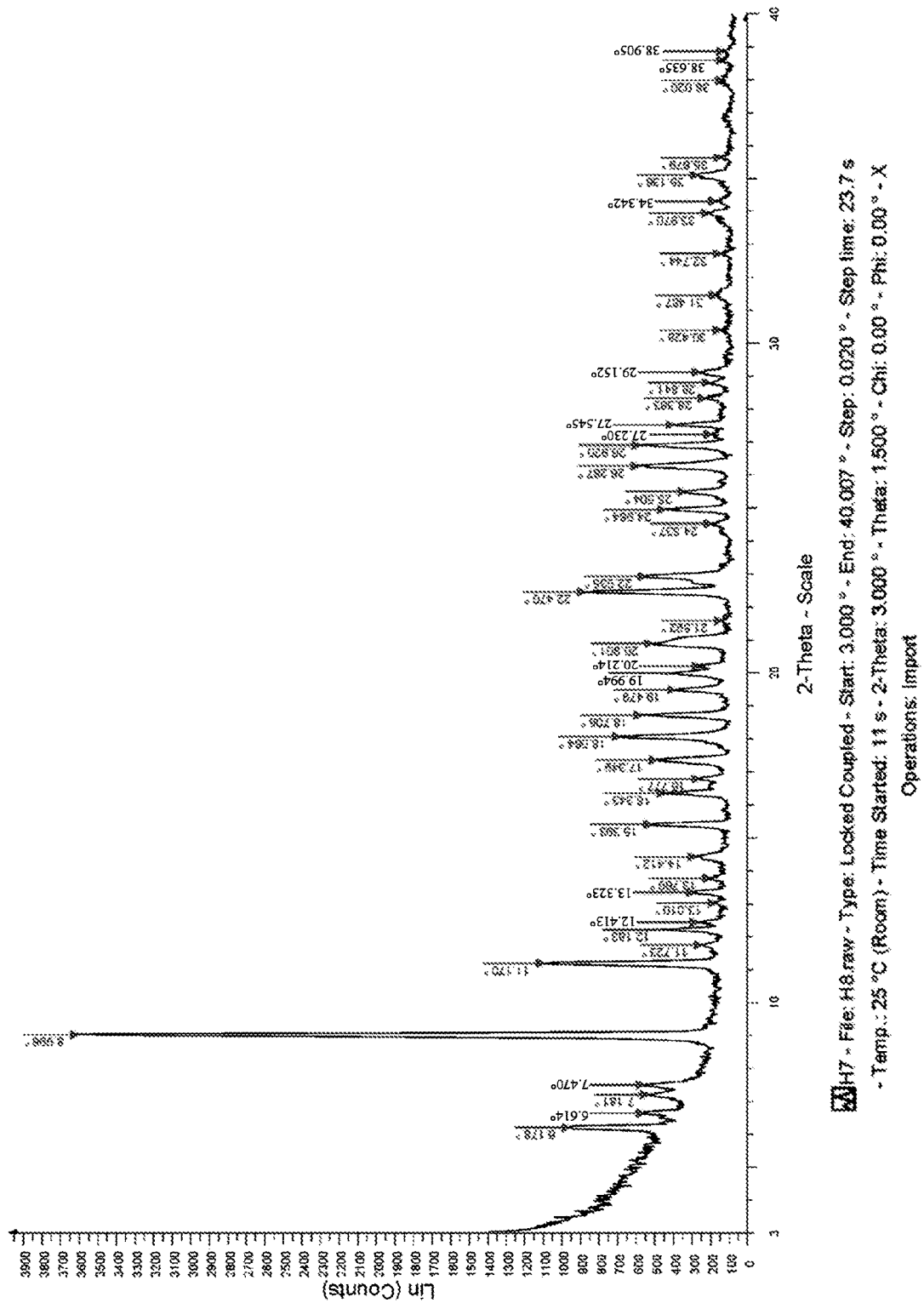
FIG. 11 is an XRPD pattern of Crystal Form IV in Example IV-1.
Figure 12:
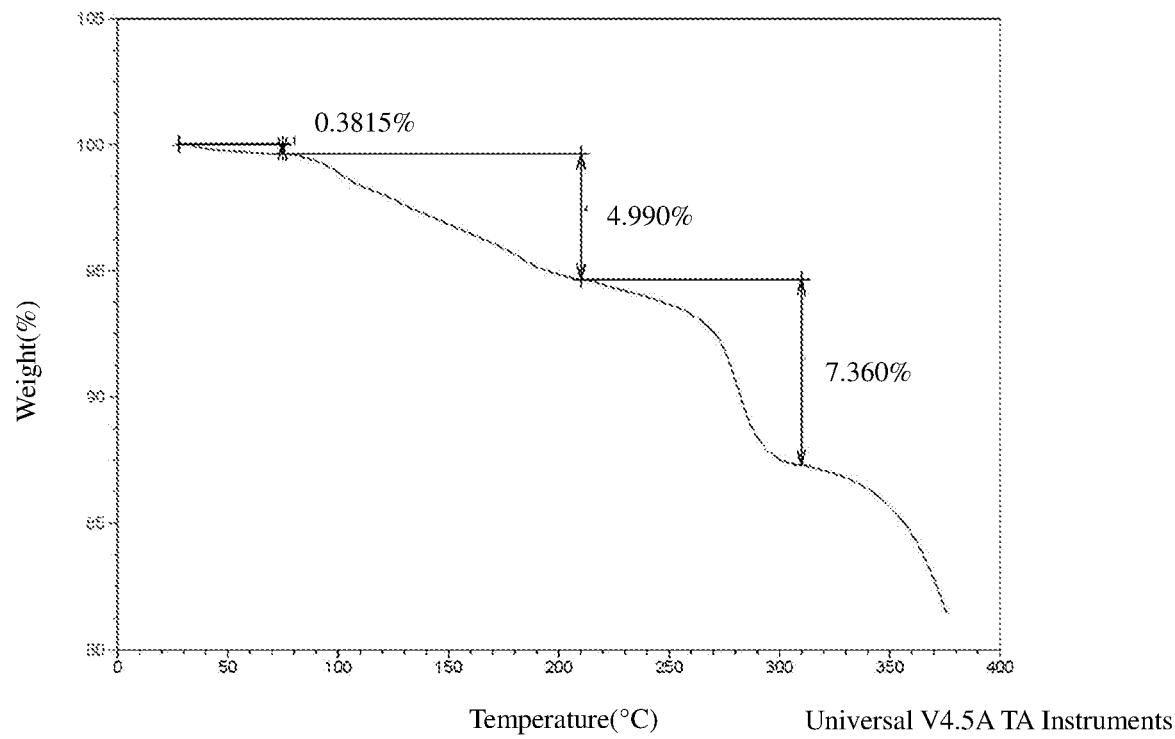
FIG. 12 is a TGA spectrum of Crystal Form IV in Example IV-1.
Figure 13:
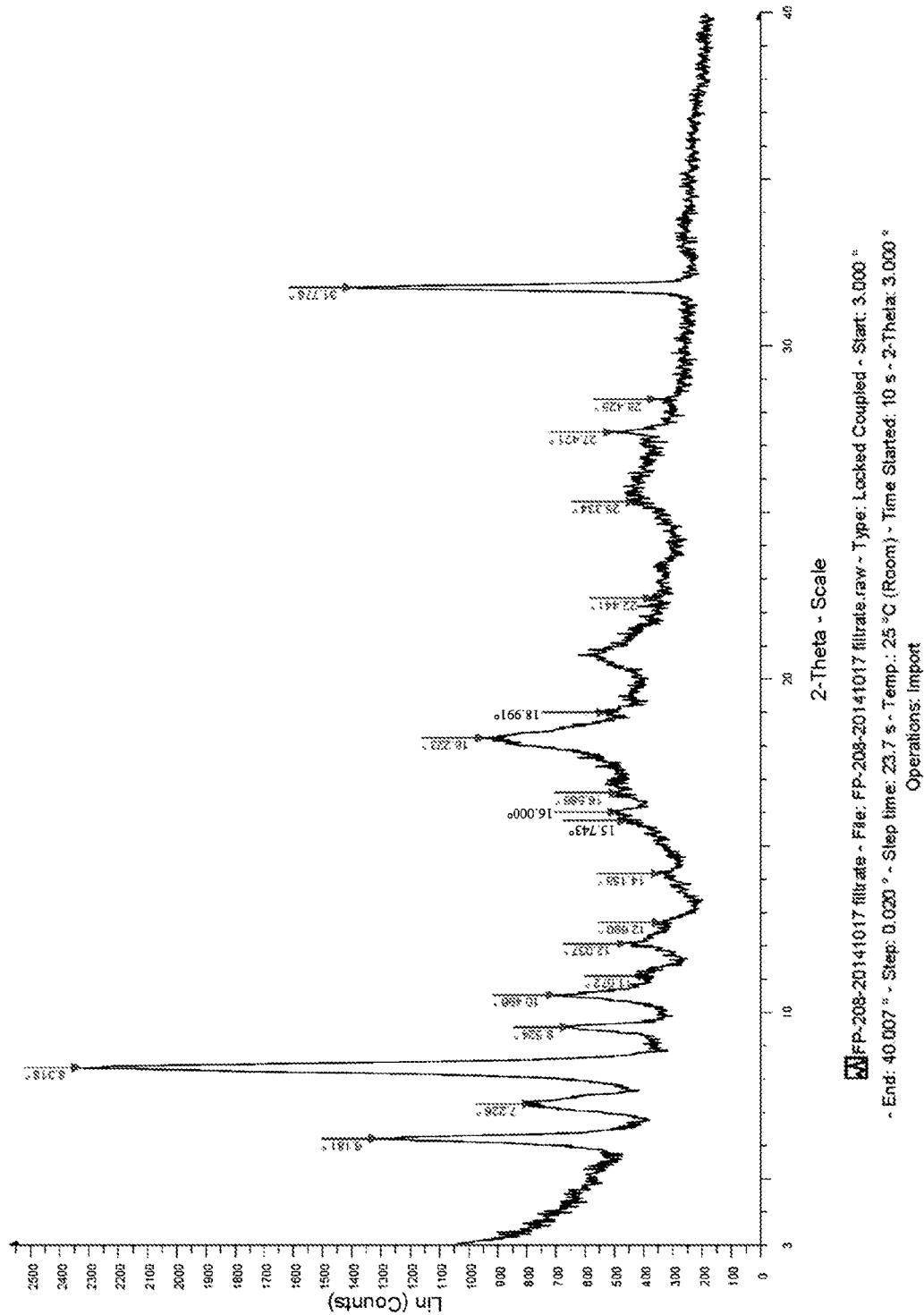
FIG. 13 is an XRPD pattern of Crystal Form V in Example V-1.
Figure 14:
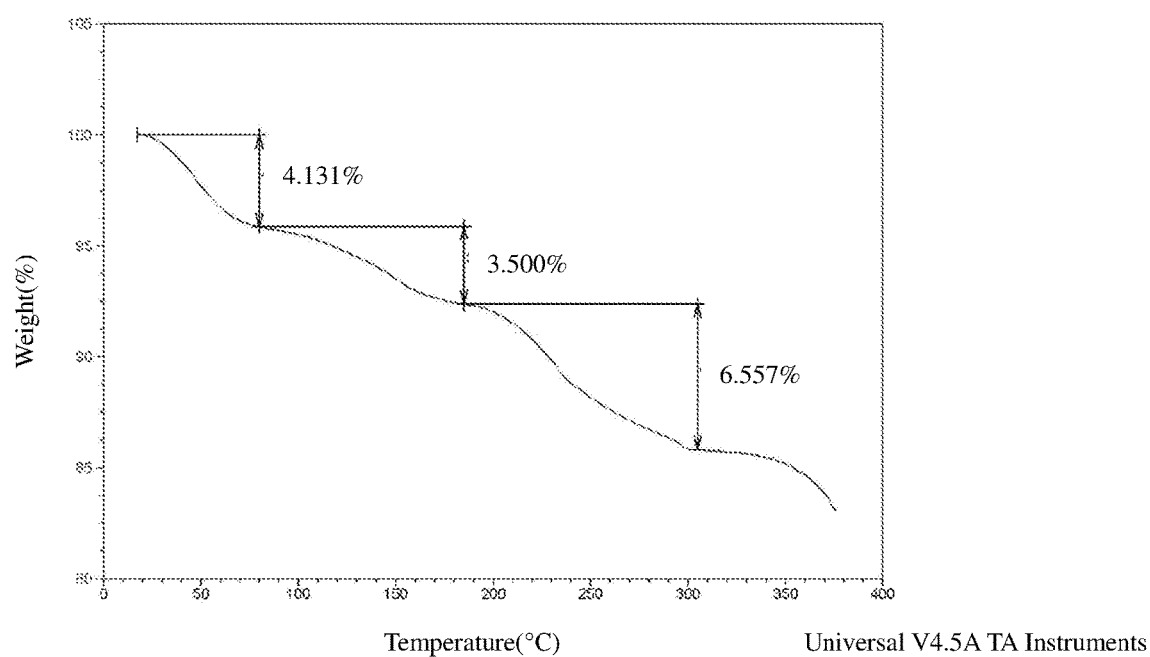
FIG. 14 is a TGA spectrum of Crystal Form V in Example V-1.
Figure 15:
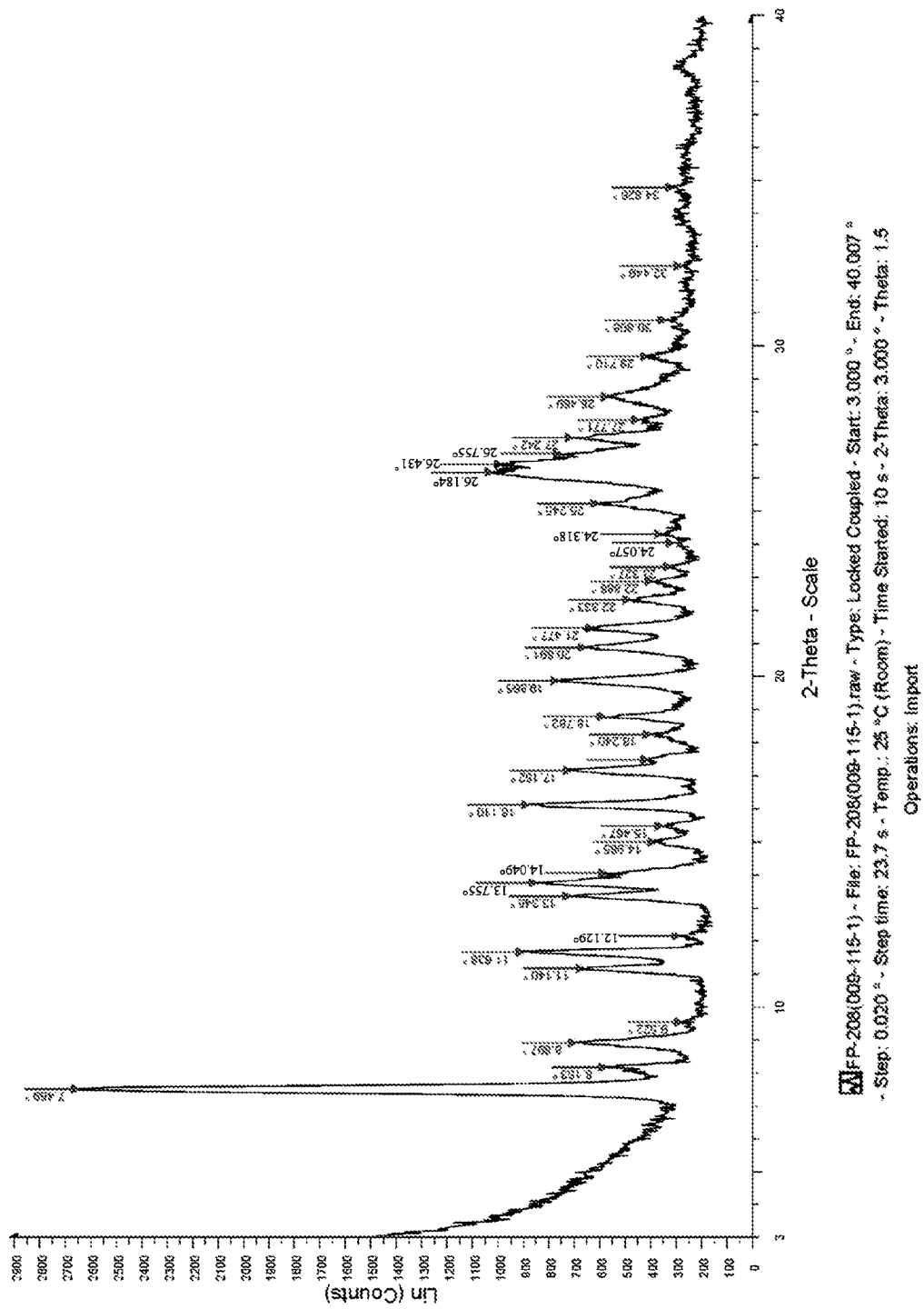
FIG. 15 is an XRPD pattern of Crystal Form VI in Example VI-1.
Figure 16:
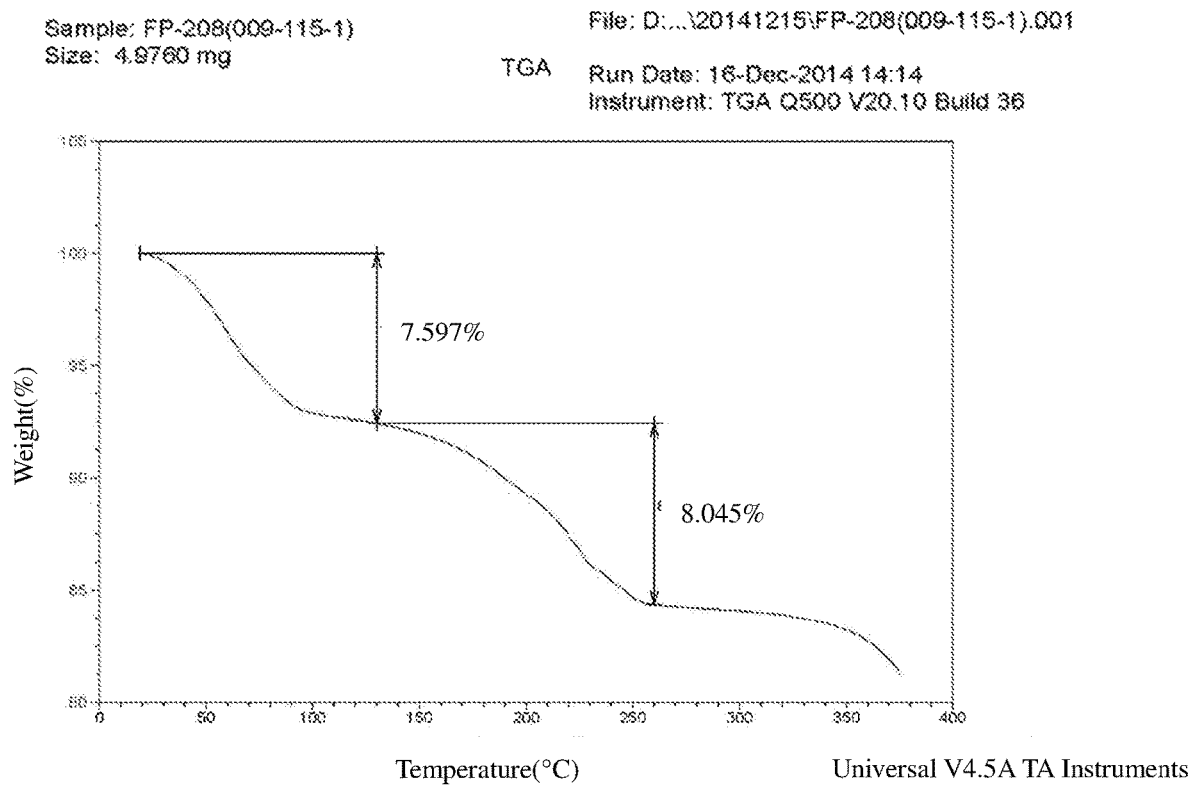
FIG. 16 is a TGA spectrum of Crystal Form VI in Example VI-1.
Figure 17:
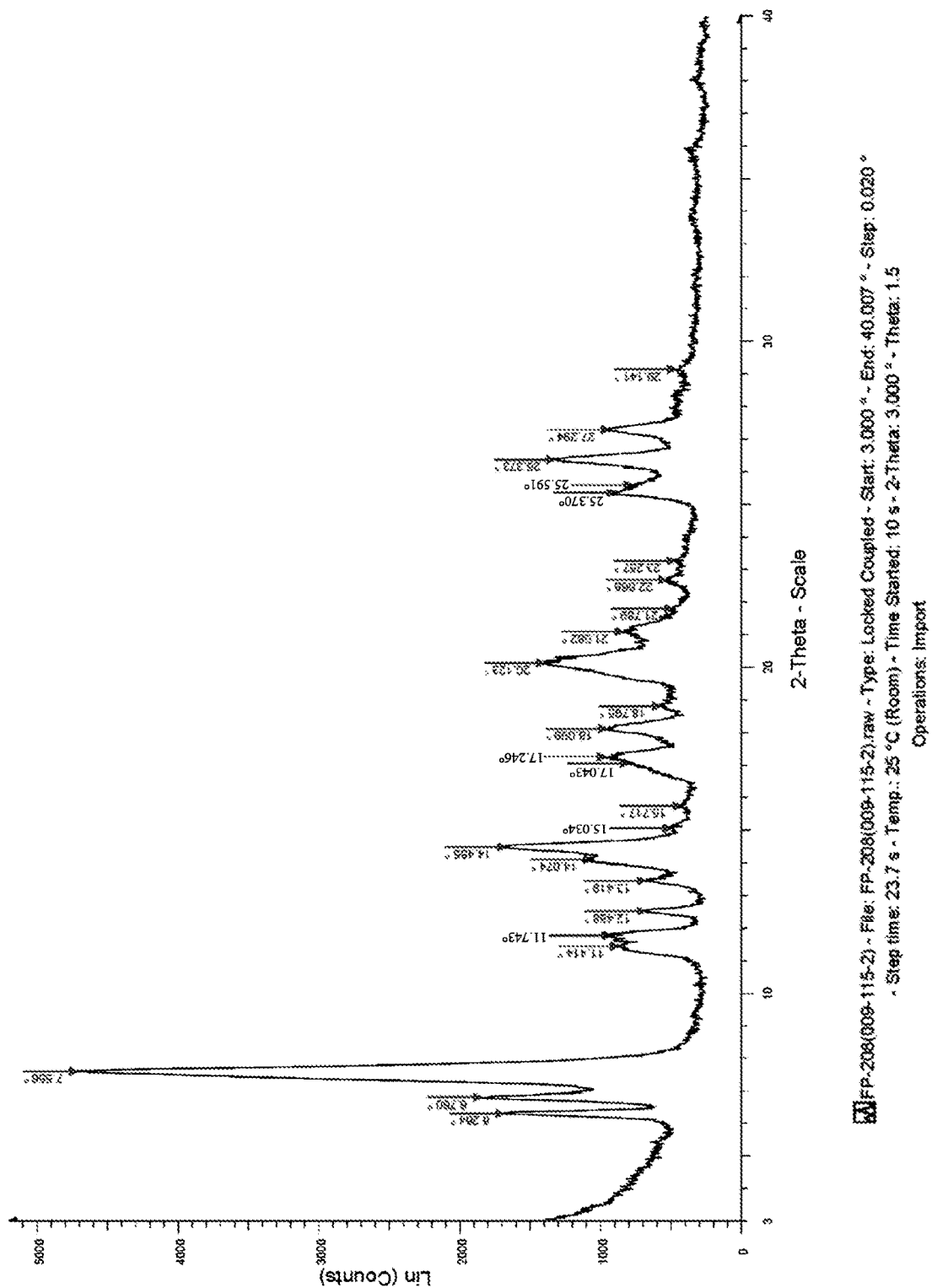
FIG. 17 is an XRPD pattern of Crystal Form VII in Example VII-1.
Figure 18:
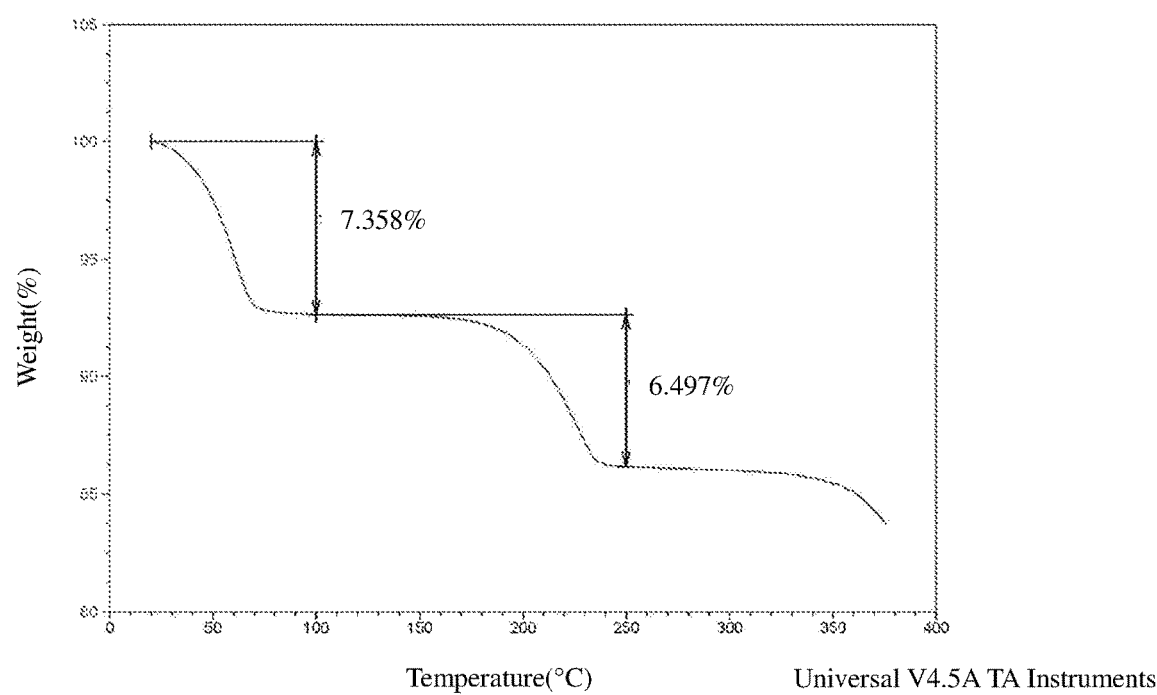
FIG. 18 is a TGA spectrum of Crystal Form VII in Example VII-1.
Figure 19:
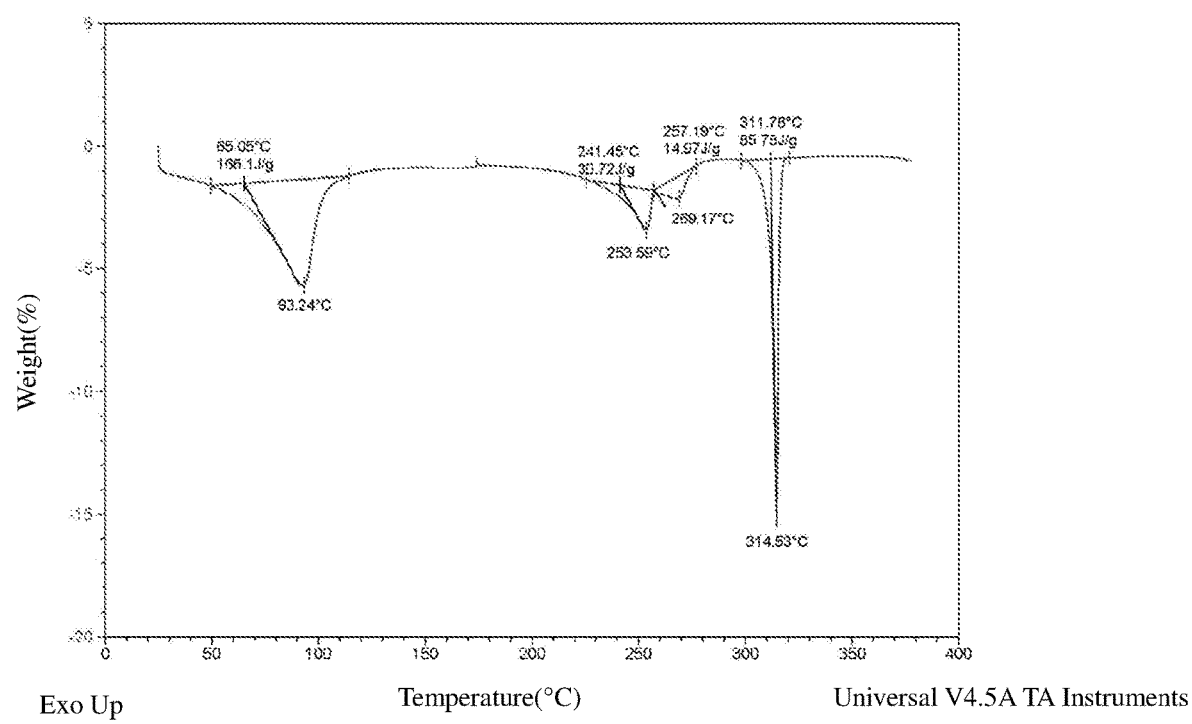
FIG. 19 is a differential scanning calorimetry (DSC) spectrum of Crystal Form VII in Example VII-1.

A small amount of Crystal Form I of Compound 1 hydrochloride monohydrate of Example 1 was taken and manually tableted to tablets with a diameter of 8 mm. The tablets were then gently ground. The powders were subjected to an XRPD analysis, and the result was compared with the XRPD result before tableting, as shown in FIG. 7, to examine whether the tableting process had an effect on the crystal form. The XRPD patterns of the powders before and after the tableting of Crystal Form I were compared. The result showed that the tableting process did not change Crystal Form I, and the XRPD patterns of the powders before and after the tableting were the same.

Example I-6: Metabolic Experiments after Oral Administration of Crystal Form I to SD Rats 11.392 mg of Crystal Form I of Compound 1 hydrochloride was suspended in 5.274 mL of 0.5% sodium carboxymethylcellulose, mixed to form a homogenous suspension, and then sonicated for 2 min to give a homogenous suspension having a concentration of 2 mg/mL (the suspension present was prepared on the day of administration, and stored for no more than 4 hours). Three SD rats were intragastrically administered at a dose of 10 mg/kg body weight, and blood analysis was performed at the set time points. The results obtained are shown in Table 1-2 below:

TABLE I-2

Metabolic experimental data after intragastric administration of Crystal Form I to rats

| Test groups | pts for $t_{1/2}$ | $t_{1/2}$ (h) | Tmax (h) | Cmax (ng/mL) | AUC last (h*ng/mL) | AUCInf (h*ng/mL) | AUC Extr (%) | MRT (h) | AUC/D (h*ng*kg/ mg*mL) |
|---|---|---|---|---|---|---|---|---|---|
| Rat 1 | 3 | 5.28 | 2.8 | 19000 | 235164 | 246808 | 4.72 | 6.74 | 11758 |
| Rat 2 | 3 | 5.40 | 4 | 12100 | 183423 | 192466 | 4.70 | 7.13 | 9171 |
| Rat 3 | 3 | 5.81 | 2.5 | 12700 | 153500 | 163230 | 5.96 | 6.65 | 7675 |
| Average | 3 | 5.50 | 3.1 | 14600 | 190696 | 200835 | 5.13 | 6.84 | 9535 |

It can be seen from Table 1-2 that after administration of the drug of Crystal Form I, the maximum plasma concentration (Cmax) can reach 14,600 ng/ml and the AUC last can reach 190696 h*ng/mL, which are very high values in drug metabolism. Meanwhile, the half-life of 5.5 hour is also an ideal value in drug metabolism. All of these prove that the drug of Crystal Form I has good absorption and metabolism properties in animals.

Example II-1: Preparation of Crystal Form II

At room temperature, 100 μl each of saturated solutions of Compound 1 hydrochloride in ethyl acetate and in 2-butanone were mixed in a 96-well plate, which was then covered with a punctured sealing film, placed in a fume hood, and naturally dried in ambient atmosphere to give crystals, which were characterized to be Crystal Form II of Compound 1 hydrochloride monohydrate.

Example II-2: Preparation of Crystal Form II

At room temperature, 100 µl each of saturated solutions of Compound 1 hydrochloride in tetrahydrofuran and in acetonitrile were mixed in a 96-well plate, which was then covered with a punctured sealing film, placed in a fume hood, and naturally dried in ambient atmosphere to give crystals, which were characterized to be Crystal Form II of Compound 1 hydrochloride monohydrate.

Example II-3: Preparation of Crystal Form II

At room temperature, 100 µl each of saturated solutions of Compound 1 hydrochloride in tetrahydrofuran and in acetone were mixed in a 96-well plate, which was then covered with a punctured sealing film, placed in a fume hood, and naturally dried in ambient atmosphere to give crystals, which were characterized to be Crystal Form II of Compound 1 hydrochloride monohydrate.

Example III-1: Preparation of Crystal Form III

At room temperature, 100 µl each of saturated solutions of Compound 1 hydrochloride in ethanol and in isopropanol were mixed in a 96-well plate, which was then covered with a punctured sealing film, placed in a fume hood, and naturally dried in ambient atmosphere to give crystals, which were characterized to be Crystal Form III of Compound 1 hydrochloride.

Example III-2: Preparation of Crystal Form III

At room temperature, 100 µl each of saturated solutions of Compound 1 hydrochloride in isopropyl alcohol and in methyl tert-butyl ether were mixed in a 96-well plate, which was then covered with a punctured sealing film, placed in a fume hood, and naturally dried in ambient atmosphere to give crystals, which were characterized to be Crystal Form III of Compound 1 hydrochloride.

Example IV-1: Preparation of Crystal Form IV

At room temperature, 100 µl each of saturated solutions of Compound 1 hydrochloride in toluene and in isobutyl acetate were mixed in a 96-well plate, which was then covered with a punctured sealing film, placed in a fume hood, and naturally dried in ambient atmosphere to give crystals, which were characterized to be Crystal Form IV of Compound 1 hydrochloride.

Example V-1: Preparation of Crystal Form V

The mother liquor from Example I-1 was allowed to stand for a prolonged time of more than 48 hours at 20-25° C. White crystals were precipitated, which were filtered by suction to give crystals, which were characterized to be Crystal Form V of Compound 1 hydrochloride dihydrate.

Example V-2: Preparation of Crystal Form V

The mother liquor from Example I-2 was allowed to stand for a prolonged time at 20-25° C. White crystals were precipitated, which were filtered by suction to give crystals, which were characterized to be Crystal Form V of Compound 1 hydrochloride dihydrate.

Example VI-1: Preparation of Crystal Form VI 0.5 g of Compound 1 hydrochloride was dissolved in a mixture of 50 ml of water and 20 ml of acetonitrile at 20-25° C. The mixture was stirred at room temperature for 20 hours. A large amount of white crystals were precipitated, which were filtered by suction. The resulting solid was dried in vacuo at 25° C. to give 0.27 g of white crystals, which were characterized to be Crystal Form VI of Compound 1 hydrochloride dihydrate.

Example VII-1: Preparation of Crystal Form VII 0.5 g of Compound 1 hydrochloride was dissolved in 90 ml of water which was heated to 90° C. The mixture was cooled down to room temperature (20-25° C.). 3 g of sodium chloride was added while stirring, followed by stirring at room temperature for 20 hours. A large amount of yellow-white solid was precipitated. After filtration by suction, the solid obtained was dried in vacuo at 25° C. to give 0.46 g of white crystals, which were characterized to be Crystal Form VII of Compound 1 hydrochloride dihydrate.

Example VII-2: Preparation of Crystal Form VII 0.5 g of Compound 1 hydrochloride was mostly dissolved in 12 ml of water which was heated to 100° C. The small amount of insolubles were removed by hot filtration, and the mother liquor was naturally cooled down to room temperature (20-25° C.) under stirring, and filtered by suction. The resulting solid was dried in vacuo at 25° C. to give 0.21 g of white crystals, which were characterized to be Crystal Form VII of Compound 1 hydrochloride dihydrate.

Example VII-3: Preparation of Crystal Form VII 10 mg of the above Crystal Form I was taken, to which was added 1 ml of water. The mixture was beaten at 20-25° C. for 3 days to give white crystals, which were characterized to be Crystal Form VII of Compound 1 hydrochloride dihydrate.

Example VII-4: Preparation of Crystal Form VII

Following Example VII-3, except that Crystal Form I was replaced with one of the above Crystal Forms II, III, IV, V and VI, Crystal Form VII is obtained.

Example VII-5: Test of Dissolution Rate of Crystal Form VII 3 mg each of Crystal Form VII, Crystal Form I, and Crystal Form VI, were weighed, and put into three 1 ml plastic centrifuge tubes, respectively. To each tube was added 1 ml of distilled water and shaken at 20-25° C. for 5 seconds. The dissolution behavior was observed:
Crystal Form VII dissolved completely within 10 seconds;
Crystal Form I dissolved substantially in 2 hours and dissolved completely in 5 hours;
Crystal Form VI failed to dissolve completely after 5 hours.

Accordingly, Crystal Form VII is an instant crystal form, which is valuable in the application of manufacturing instant dosage forms.

What is claimed is:

1. A crystal of a pharmaceutically acceptable salt of Compound 1 represented by the following formula or a hydrate thereof:

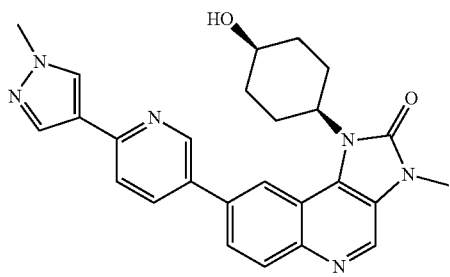

Compound 1 wherein (a) said crystal is Crystal Form I of Compound 1 hydrochloride monohydrate, which is characterized by an X-ray powder diffraction pattern obtained by using Cu-Kα radiation, which diffraction pattern comprises characteristic peaks expressed in 2-theta angle (°) at:
9.028±0.2, 11.196±0.2, 17.393±0.2, 22.504±0.2; or
9.028±0.2, 11.196±0.2, 15.406±0.2, 16.380±0.2, 17.393±0.2, 18.066±0.2, 18.739±0.2, 20.894±0.2, 22.504±0.2, 22.955±0.2; or
9.028±0.2, 11.196±0.2, 15.406±0.2, 16.380±0.2, 17.393±0.2, 18.066±0.2, 18.739±0.2, 20.894±0.2, 22.504±0.2, 22.955±0.2, 26.312±0.2, 26.918±0.2, 27.556±0.2, 35.168±0.2; or
9.028±0.2, 11.196±0.2, 12.200±0.2, 15.406±0.2, 16.380±0.2, 16.828±0.2, 17.393±0.2, 18.066±0.2, 18.739±0.2, 20.036±0.2, 20.894±0.2, 22.504±0.2, 22.955±0.2, 24.973±0.2, 25.505±0.2, 26.312±0.2, 26.918±0.2, 27.556±0.2, 28.403±0.2, 29.176±0.2, 31.586±0.2, 35.168±0.2;

or (b) said crystal is Crystal Form II of Compound 1 hydrochloride monohydrate, which is characterized by an X-ray powder diffraction pattern obtained by using Cu-Kα radiation, which diffraction pattern comprises characteristic peaks expressed in 2-theta angle (°) at:
8.934±0.2, 11.126±0.2, 15.367±0.2, 22.437±0.2; or
8.934±0.2, 11.126±0.2, 12.161±0.2, 15.367±0.2, 16.289±0.2, 17.369±0.2, 18.037±0.2, 18.667±0.2, 20.896±0.2, 22.437±0.2, 22.928±0.2, 24.995±0.2, 26.269±0.2, 26.890±0.2, 27.574±0.2; or
8.486±0.2, 8.934±0.2, 11.126±0.2, 12.161±0.2, 13.317±0.2 15.367±0.2, 16.289±0.2, 16.742±0.2, 17.369±0.2, 18.037±0.2, 18.667±0.2, 19.966±0.2, 20.896±0.2, 22.437±0.2, 22.928±0.2, 24.995±0.2, 25.467±0.2, 26.269±0.2, 26.890±0.2, 27.213±0.2, 27.574±0.2, 28.366±0.2, 29.075±0.2, 35.001±0.2;

or (c) said crystal is Crystal Form III of Compound 1 hydrochloride, which is characterized by an X-ray powder diffraction pattern obtained by using Cu-Kα radiation, which diffraction pattern comprises characteristic peaks expressed in 2-theta angle (°) at:
6.396±0.2, 7.115±0.2, 8.972±0.2, 10.803±0.2, 11.870±0.2, 18.542±0.2, 23.071±0.2; or
6.396±0.2, 7.115±0.2, 8.972±0.2, 10.803±0.2, 11.147±0.2, 11.870±0.2, 12.139±0.2, 15.417±0.2, 16.297±0.2, 16.559±0.2, 17.374±0.2, 18.074±0.2, 18.542±0.2, 19.310±0.2, 22.464±0.2, 23.071±0.2, 24.550±0.2, 25.843±0.2, 26.903±0.2, 28.737±0.2, 29.664±0.2, 35.016±0.2;

or (d) said crystal is Crystal Form IV of Compound 1 hydrochloride, which is characterized by an X-ray powder diffraction pattern obtained by using Cu-Kα radiation, which diffraction pattern comprises characteristic peaks expressed in 2-theta angle (°) at:
6.178±0.2, 8.996±0.2, 11.170±0.2, 15.393±0.2, 16.343±0.2, 17.349±0.2, 18.064±0.2, 18.708±0.2, 19.479±0.2, 19.994±0.2, 20.901±0.2, 22.470±0.2, 22.935±0.2, 24.964±0.2, 25.504±0.2, 26.287±0.2, 26.920±0.2, 27.545±0.2; or
6.178±0.2, 6.614±0.2, 7.181±0.2, 7.470±0.2, 8.996±0.2, 11.170±0.2, 11.723±0.2, 12.183±0.2, 13.323±0.2, 14.412±0.2, 15.393±0.2, 16.343±0.2, 16.777±0.2, 17.349±0.2, 18.064±0.2, 18.708±0.2, 19.479±0.2, 19.994±0.2, 20.901±0.2, 22.470±0.2, 22.935±0.2, 24.964±0.2, 25.504±0.2, 26.287±0.2, 26.920±0.2, 27.545±0.2, 28.363±0.2, 28.841±0.2, 29.152±0.2, 31.487±0.2, 33.970±0.2, 35.136±0.2;

or (e) said crystal is Crystal Form V of Compound 1 hydrochloride dihydrate, which is characterized by an X-ray powder diffraction pattern obtained by using Cu-Kα radiation, which diffraction pattern comprises characteristic peaks expressed in 2-theta angle (°) at:
6.181±0.2, 8.318±0.2, 18.223±0.2, 31.778±0.2; or
6.181±0.2, 7.226±0.2, 8.318±0.2, 9.524±0.2, 10.496±0.2, 12.037±0.2, 18.223±0.2, 27.421±0.2, 31.778±0.2;

or (f) said crystal is Crystal Form VI of Compound 1 hydrochloride dihydrate, which is characterized by an X-ray powder diffraction pattern obtained by using Cu-Kα radiation, which diffraction pattern comprises characteristic peaks expressed in 2-theta angle (°) at:
7.489±0.2, 8.897±0.2, 11.140±0.2, 11.638±0.2, 13.348±0.2, 13.755±0.2, 16.110±0.2, 17.152±0.2, 18.782±0.2, 19.865±0.2, 20.891±0.2, 21.477±0.2, 25.245±0.2, 26.184±0.2, 26.431±0.2, 27.242±0.2, 28.489±0.2; or
7.489±0.2, 8.153±0.2, 8.897±0.2, 11.140±0.2, 11.638±0.2, 13.348±0.2, 13.755±0.2, 14.985±0.2, 15.467±0.2, 16.110±0.2, 17.152±0.2, 18.240±0.2, 18.782±0.2, 19.865±0.2, 20.891±0.2, 21.477±0.2, 22.333±0.2, 22.888±0.2, 25.245±0.2, 26.184±0.2, 26.431±0.2, 27.242±0.2, 28.489±0.2, 29.710±0.2;

or (g) said crystal is Crystal Form VII of Compound 1 hydrochloride dihydrate, which is characterized by an X-ray powder diffraction pattern obtained by using Cu-Kα radiation, which diffraction pattern comprises characteristic peaks expressed in 2-theta angle (°) at:
6.264±0.2, 6.760±0.2, 7.556±0.2, 14.455±0.2, 20.123±0.2, 26.373±0.2; or
6.264±0.2, 6.760±0.2, 7.556±0.2, 11.414±0.2, 11.743±0.2, 12.488±0.2, 13.419±0.2, 14.455±0.2, 17.246±0.2, 18.099±0.2, 20.123±0.2, 21.082±0.2, 25.370±0.2, 26.373±0.2, 27.294±0.2.

2. A pharmaceutical composition comprising the crystal according to claim 1 and at least one pharmaceutically acceptable carrier or auxiliary.

3. The crystal of claim 1, wherein said crystal is Crystal Form I of Compound 1 hydrochloride monohydrate.

4. A method for preparing the crystal according to claim 3, which is one of the following preparation methods A and B:

preparation method A, comprising:
1) dissolving Compound 1 hydrochloride in water;
2) adding sodium chloride to the solution of step 1); and
3) cooling down, crystallizing, filtering, and drying to give Crystal Form I,
wherein in step 1), water is heated before or after the addition of Compound 1 hydrochloride to dissolve Compound 1 hydrochloride; wherein water is used in an amount 2-80 times the weight of Compound 1 hydrochloride; and the water is heated to 70-100° C.;
wherein in step 2), sodium chloride is added while maintaining the temperature of the solution of step 1); the amount of sodium chloride is controlled so that it makes up 0.1-26% of the total weight of the solution;
wherein the weight percentage content of sodium chloride is in the range from 10% to the saturated concentration;
wherein in step 3), the mixture is slowly cooled down to below 60° C. under stirring to crystallize, followed by filtration by suction, rinsing, and drying in vacuo at 15-35° C. to give Crystal Form I of Compound 1 hydrochloride monohydrate;
or,
preparation method B, comprising:
1) dissolving Compound 1 hydrochloride in an aqueous solution of ethanol; and
2) cooling down, crystallizing, filtering, and drying to give Crystal Form I;
wherein in step 1), the aqueous solution of ethanol is heated before or after the addition of Compound 1 hydrochloride to dissolve Compound 1 hydrochloride; wherein the amount of the aqueous solution of ethanol is 5-80 times the weight of Compound 1 hydrochloride; and the aqueous solution of ethanol is heated to 50-100° C.;
wherein the mass percentage of ethanol in the aqueous solution of ethanol is 30 to 99%;
wherein in step 2), the mixture is slowly cooled down to below 40° C. under stirring to crystallize, followed by filtration by suction, and drying in vacuo at 15 to 35° C. to give Crystal Form I of Compound 1 hydrochloride monohydrate.

5. The crystal of claim 1, wherein said crystal is Crystal Form II of Compound 1 hydrochloride monohydrate.

6. The crystal of claim 1, wherein said crystal is Crystal Form III of Compound 1 hydrochloride.

7. The crystal of claim 1, wherein said crystal is Crystal Form IV of Compound 1 hydrochloride.

8. The crystal of claim 1, wherein said crystal is Crystal Form V of Compound 1 hydrochloride dihydrate.

9. The crystal of claim 1, wherein said crystal is Crystal Form VI of Compound 1 hydrochloride dihydrate.

10. The crystal of claim 1, wherein said crystal is Crystal Form VII of Compound 1 hydrochloride dihydrate.

11. A method for preparing the crystal according to claim 10, which is one of the following preparation methods A and B:

preparation method A, comprising:
1) dissolving Compound 1 hydrochloride in water;
2a) cooling the aqueous solution of step 1) to crystallize; or 2b) adding sodium chloride to the aqueous solution of step 1) and stirring to crystallize; and
3) filtering, and drying, to give Crystal Form VII;
wherein in step 1), the amount of water used is 10 to 500 times the weight of Compound 1 hydrochloride; water is heated before or after Compound 1 hydrochloride is added; a step of hot filtration to remove insolubles is optionally included; and the water is heated to 70-100° C.;
wherein in step 2a), the aqueous solution of step 1) is cooled down to below 40° C. to crystallize;
wherein in step 2b), the solution is stirred at below 40° C. crystallize; and the amount of sodium chloride is 1 to 15 times that of Compound 1 hydrochloride;
wherein in step 3), the filtering is by suction, and the drying is in vacuo;
or,
preparation method B, comprising:
mixing and beating one or more of the Crystal Forms I-VI with water for 3 days to give Crystal Form VII;
wherein the mixing and beating are performed at below 40° C.; and the amount of water used in the mixing and beating is 20 to 200 times the total weight of Crystal Forms I-VI.

12. A pharmaceutical composition comprising the crystal according to claim 3 and at least one pharmaceutically acceptable carrier or auxiliary.

13. A pharmaceutical composition comprising the crystal according to claim 5 and at least one pharmaceutically acceptable carrier or auxiliary.

14. A pharmaceutical composition comprising the crystal according to claim 6 and at least one pharmaceutically acceptable carrier or auxiliary.

15. A pharmaceutical composition comprising the crystal according to claim 7 and at least one pharmaceutically acceptable carrier or auxiliary.

16. A pharmaceutical composition comprising the crystal according to claim 8 and at least one pharmaceutically acceptable carrier or auxiliary.

17. A pharmaceutical composition comprising the crystal according to claim 9 and at least one pharmaceutically acceptable carrier or auxiliary.

18. A pharmaceutical composition comprising the crystal according to claim 10 and at least one pharmaceutically acceptable carrier or auxiliary.

* * * * *